(12) United States Patent
Kamo et al.

(10) Patent No.: US 7,510,525 B2
(45) Date of Patent: Mar. 31, 2009

(54) SYSTEM FOR TOPICAL NERVE DIAGNOSIS AND NEUROANATOMICAL STUDY

(75) Inventors: Hisaki Kamo, Kyoto (JP); Naoki Okada, Kyoto (JP)

(73) Assignee: Hisaki Kamo, Kyoto (JP)

( * ) Notice: Subject to any disclaimer, the term of this patent is extended or adjusted under 35 U.S.C. 154(b) by 552 days.

(21) Appl. No.: 10/510,926

(22) PCT Filed: Feb. 26, 2004

(86) PCT No.: PCT/JP2004/002327

§ 371 (c)(1),
(2), (4) Date: Oct. 8, 2004

(87) PCT Pub. No.: WO2004/080311

PCT Pub. Date: Sep. 23, 2004

(65) Prior Publication Data

US 2006/0079738 A1  Apr. 13, 2006

(30) Foreign Application Priority Data

Mar. 10, 2003 (JP) .............................. 2003-063876
Dec. 1, 2003 (JP) .............................. 2003-402116

(51) Int. Cl.
*A61B 5/00* (2006.01)
*A61B 19/00* (2006.01)
*A61B 5/04* (2006.01)

(52) U.S. Cl. ..................... 600/300; 600/301; 126/897

(58) Field of Classification Search ................ 600/300, 600/301; 128/920, 898, 897
See application file for complete search history.

(56) References Cited

U.S. PATENT DOCUMENTS 6,249,594 B1 * 6/2001 Hibbard ...................... 382/128
6,925,199 B2 * 8/2005 Murao ......................... 382/131

FOREIGN PATENT DOCUMENTS

| JP | 62-148645 A | 7/1987 |
| JP | 4-503622 A | 6/1991 |
| JP | 10-225521 A | 8/1998 |
| WO | WO 91/08702 | 6/1991 |
| WO | WO 9317614 A1 * | 9/1993 |

* cited by examiner

*Primary Examiner*—Max Hindenburg
*Assistant Examiner*—John Pani
(74) *Attorney, Agent, or Firm*—Hodgson Russ LLP

(57) ABSTRACT

A system having a whole nerve pathway diagram data recording unit 1; a nerve finding data input unit 2; a responsible nerve pathway data extraction unit 3 by which the data of a nerve pathway responsible for a nerve finding item showing an abnormal finding is extracted from the data of the whole nerve pathway diagram data recording unit based on the data obtained by the nerve finding input unit; a whole nerve pathway indication unit 5 by which the whole nerve pathway is indicated in a display unit 4 based on the data of the whole nerve pathway diagram data recording unit; a responsible nerve pathway indication unit 6 by which the responsible nerve pathway is indicated in the whole nerve pathway diagram based on the data of the whole nerve pathway diagram data recording unit; and a responsible lesion estimation/indication unit 7 by which the location of the responsible lesion in the whole nerve pathway diagram is estimated and indicated in the whole nerve pathway diagram based on the data of the responsible nerve pathway shown in the display unit.

11 Claims, 21 Drawing Sheets

Fig. 2

| Neural Finding Item | Right | Left |
|---|---|---|
| Oculomotor Restriction | No | No |
| Inferior Oculomotor Restriction | No | No |
| Jaw Reflex Acceleration | No | No |
| Impaired Facial Tactual Senstaion | No | No |
| Impaired Facial Pain/Temperature Sensation | No | No |
| Corneal Areflexia | No | No |
| Exterior Oculomotor Restriction No | No | No |
| Upper Facial Paralysis | No | No |
| Lower Facial Paralysis | No | No |
| Impaired Taste | No | No |
| Lowered Pharyngeal Reflex/Swallowing Difficulty | No | No |
| Impaired Pharyngeal Sound Dysphemia | No | No |
| Lingual Muscle Paralysis/Impaired Lingual Sound Dysphemia | No | No |
| Sternocleidomastoid Paralysis | No | No |
| Impaired Upper Limb Pain/Temperature Sensation | No | No |
| Impaired Upper Limb Deep Sensation | No | No |
| Upper Limb Motor Paralysis | Yes | No |
| Upper Limb Tendon Reflex Acceleration No | No | No |
| Impaired Trunk Pain/Temperature Sensation | No | No |
| Impaired Trunk Deep Sensation | No | No |
| Level Of Impaired Trunk Deep Sensation | No | No |
| Impaired Lower Limb Pain/Temperature Sensation | No | No |
| Impaired Lower Limb Deep Sensation | No | No |
| Lower Limb Motor paralysis | No | No |
| Lower Limb Tendon Reflex Acceleration No | No | No |
| Babinsky's Reflex | No | No |

Fig. 3

| Neural Finding Item | Right | Left |
|---|---|---|
| Oculomotor Restriction | No | No |
| Inferior Oculomotor Restriction | No | No |
| Jaw Reflex Acceleration | No | No |
| Impaired Facial Tactual Senstaion | No | No |
| Impaired Facial Pain/Temperature Sensation | No | No |
| Corneal Areflexia | No | No |
| Exterior Oculomotor Restriction No | No | No |
| Upper Facial Paralysis | No | No |
| Lower Facial Paralysis | No | No |
| Impaired Taste | No | No |
| Lowered Pharyngeal Reflex/Swallowing Difficulty | No | No |
| Impaired Pharyngeal Sound Dysphemia | No | No |
| Lingual Muscle Paralysis/Impaired Lingual Sound Dysphemia | No | No |
| Sternocleidomastoid Paralysis | No | No |
| Impaired Upper Limb Pain/Temperature Sensation | No | No |
| Impaired Upper Limb Deep Sensation | No | No |
| Upper Limb Motor Paralysis | Yes | No |
| Upper Limb Tendon Reflex Acceleration No | No | No |
| Impaired Trunk Pain/Temperature Sensation | No | No |
| Impaired Trunk Deep Sensation | No | No |
| Level Of Impaired Trunk Deep Sensation | No | No |
| Impaired Lower Limb Pain/Temperature Sensation | No | No |
| Impaired Lower Limb Deep Sensation | No | No |
| Lower Limb Motor paralysis | Yes | No |
| Lower Limb Tendon Reflex Acceleration No | No | No |
| Babinsky's Reflex | No | No |

Columns: 21 (Neural Finding Item), 22 (Right), 23 (Left); Table: 20

Fig. 4

| Neural Finding Item | Right | Left |
|---|---|---|
| Oculomotor Restriction | No | No |
| Inferior Oculomotor Restriction | No | No |
| Jaw Reflex Acceleration | No | No |
| Impaired Facial Tactual Senstaion | No | No |
| Impaired Facial Pain/Temperature Sensation | No | No |
| Corneal Areflexia | No | No |
| Exterior Oculomotor Restriction No | No | No |
| Upper Facial Paralysis | No | Yes |
| Lower Facial Paralysis | No | No |
| Impaired Taste | No | No |
| Lowered Pharyngeal Reflex/Swallowing Difficulty | No | No |
| Impaired Pharyngeal Sound Dysphemia | No | No |
| Lingual Muscle Paralysis/Impaired Lingual Sound Dysphemia | No | No |
| Sternocleidomastoid Paralysis | No | No |
| Impaired Upper Limb Pain/Temperature Sensation | No | No |
| Impaired Upper Limb Deep Sensation | No | No |
| Upper Limb Motor Paralysis | Yes | No |
| Upper Limb Tendon Reflex Acceleration No | No | No |
| Impaired Trunk Pain/Temperature Sensation | No | No |
| Impaired Trunk Deep Sensation | No | No |
| Level Of Impaired Trunk Deep Sensation | No | No |
| Impaired Lower Limb Pain/Temperature Sensation | No | No |
| Impaired Lower Limb Deep Sensation | No | No |
| Lower Limb Motor paralysis | Yes | No |
| Lower Limb Tendon Reflex Acceleration No | No | No |
| Babinsky's Reflex | No | No |

Fig. 5

| Neural Finding Item | Right | Left |
|---|---|---|
| Oculomotor Restriction | No | No |
| Inferior Oculomotor Restriction | No | No |
| Jaw Reflex Acceleration | No | No |
| Impaired Facial Tactual Senstaion | No | No |
| Impaired Facial Pain/Temperature Sensation | No | No |
| Corneal Areflexia | No | No |
| Exterior Oculomotor Restriction No | No | Yes |
| Upper Facial Paralysis | No | Yes |
| Lower Facial Paralysis | No | No |
| Impaired Taste | No | No |
| Lowered Pharyngeal Reflex/Swallowing Difficulty | No | No |
| Impaired Pharyngeal Sound Dysphemia | No | No |
| Lingual Muscle Paralysis/Impaired Lingual Sound Dysphemia | No | No |
| Sternocleidomastoid Paralysis | No | No |
| Impaired Upper Limb Pain/Temperature Sensation | No | No |
| Impaired Upper Limb Deep Sensation | No | No |
| Upper Limb Motor Paralysis | Yes | No |
| Upper Limb Tendon Reflex Acceleration No | No | No |
| Impaired Trunk Pain/Temperature Sensation | No | No |
| Impaired Trunk Deep Sensation | No | No |
| Level Of Impaired Trunk Deep Sensation | No | No |
| Impaired Lower Limb Pain/Temperature Sensation | No | No |
| Impaired Lower Limb Deep Sensation | No | No |
| Lower Limb Motor paralysis | Yes | No |
| Lower Limb Tendon Reflex Acceleration No | No | No |
| Babinsky's Reflex | No | No |

Fig. 6

| | 21 | 22 | 23 |
|---|---|---|---|
| Neural Finding Item | | Right | Left |
| Oculomotor Restriction | | No | No |
| Inferior Oculomotor Restriction | | No | No |
| Jaw Reflex Acceleration | | No | No |
| Impaired Facial Tactual Senstaion | | No | No |
| Impaired Facial Pain/Temperature Sensation | | No | No |
| Corneal Areflexia | | No | No |
| Exterior Oculomotor Restriction No | | No | Yes |
| Upper Facial Paralysis | | No | Yes |
| Lower Facial Paralysis | | No | No |
| Impaired Taste | | No | No |
| Lowered Pharyngeal Reflex/Swallowing Difficulty | | No | No |
| Impaired Pharyngeal Sound Dysphemia | | No | No |
| Lingual Muscle Paralysis/Impaired Lingual Sound Dysphemia | | No | No |
| Sternocleidomastoid Paralysis | | No | No |
| Impaired Upper Limb Pain/Temperature Sensation | | No | No |
| Impaired Upper Limb Deep Sensation | | No | No |
| Upper Limb Motor Paralysis | | Yes | No |
| Upper Limb Tendon Reflex Acceleration No | | Yes | No |
| Impaired Trunk Pain/Temperature Sensation | | No | No |
| Impaired Trunk Deep Sensation | | No | No |
| Level Of Impaired Trunk Deep Sensation | | No | No |
| Impaired Lower Limb Pain/Temperature Sensation | | No | No |
| Impaired Lower Limb Deep Sensation | | No | No |
| Lower Limb Motor paralysis | | Yes | No |
| Lower Limb Tendon Reflex Acceleration No | | No | No |
| Babinsky's Reflex | | No | No |

Fig. 7

| Neural Finding Item | Right | Left |
|---|---|---|
| Oculomotor Restriction | No | No |
| Inferior Oculomotor Restriction | No | No |
| Jaw Reflex Acceleration | No | No |
| Impaired Facial Tactual Senstaion | No | No |
| Impaired Facial Pain/Temperature Sensation | No | No |
| Corneal Areflexia | No | No |
| Exterior Oculomotor Restriction No | No | Yes |
| Upper Facial Paralysis | No | Yes |
| Lower Facial Paralysis | No | No |
| Impaired Taste | No | No |
| Lowered Pharyngeal Reflex/Swallowing Difficulty | No | No |
| Impaired Pharyngeal Sound Dysphemia | No | No |
| Lingual Muscle Paralysis/Impaired Lingual Sound Dysphemia | No | No |
| Sternocleidomastoid Paralysis | No | No |
| Impaired Upper Limb Pain/Temperature Sensation | No | No |
| Impaired Upper Limb Deep Sensation | No | No |
| Upper Limb Motor Paralysis | Yes | No |
| Upper Limb Tendon Reflex Acceleration No | Yes | No |
| Impaired Trunk Pain/Temperature Sensation | No | No |
| Impaired Trunk Deep Sensation | No | No |
| Level Of Impaired Trunk Deep Sensation | No | No |
| Impaired Lower Limb Pain/Temperature Sensation | No | No |
| Impaired Lower Limb Deep Sensation | No | No |
| Lower Limb Motor paralysis | Yes | No |
| Lower Limb Tendon Reflex Acceleration No | Yes | No |
| Babinsky's Reflex | No | No |

Fig. 8

| Neural Finding Item | Right | Left |
|---|---|---|
| Oculomotor Restriction | No | No |
| Inferior Oculomotor Restriction | No | No |
| Jaw Reflex Acceleration | No | No |
| Impaired Facial Tactual Senstaion | No | No |
| Impaired Facial Pain/Temperature Sensation | No | No |
| Corneal Areflexia | No | No |
| Exterior Oculomotor Restriction No | No | Yes |
| Upper Facial Paralysis | No | Yes |
| Lower Facial Paralysis | No | No |
| Impaired Taste | No | No |
| Lowered Pharyngeal Reflex/Swallowing Difficulty | No | No |
| Impaired Pharyngeal Sound Dysphemia | No | No |
| Lingual Muscle Paralysis/Impaired Lingual Sound Dysphemia | No | No |
| Sternocleidomastoid Paralysis | No | No |
| Impaired Upper Limb Pain/Temperature Sensation | No | No |
| Impaired Upper Limb Deep Sensation | No | No |
| Upper Limb Motor Paralysis | Yes | No |
| Upper Limb Tendon Reflex Acceleration No | Yes | No |
| Impaired Trunk Pain/Temperature Sensation | No | No |
| Impaired Trunk Deep Sensation | No | No |
| Level Of Impaired Trunk Deep Sensation | No | No |
| Impaired Lower Limb Pain/Temperature Sensation | No | No |
| Impaired Lower Limb Deep Sensation | No | No |
| Lower Limb Motor paralysis | Yes | No |
| Lower Limb Tendon Reflex Acceleration No | Yes | No |
| Babinsky's Reflex | Yes | No |

Nerve pathway

- Sympathetic nerve pathway — 50
- Visual sense pathway — 51
- Acoustic sense pathway — 52
- Motor nerve (cone) pathway — 53
- Perception pathway — 54

Fig. 20
Fig. 21
From Fig. 19
From Fig. 20
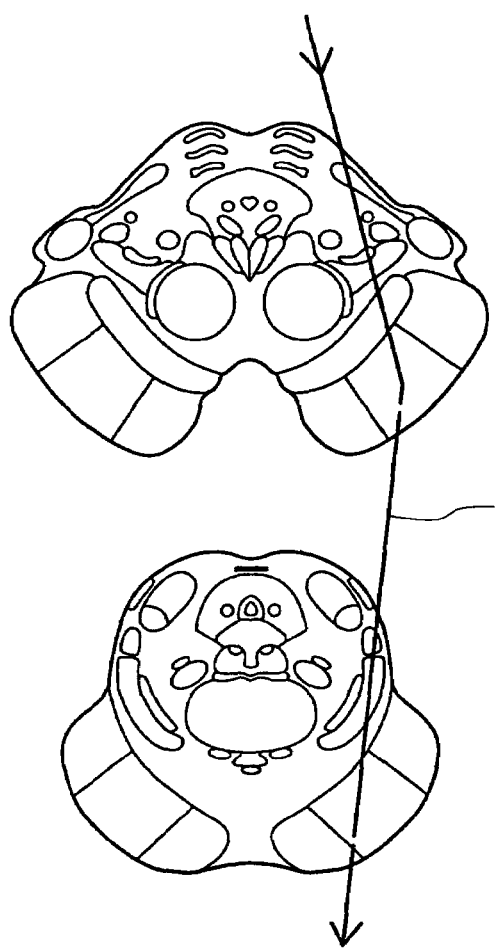
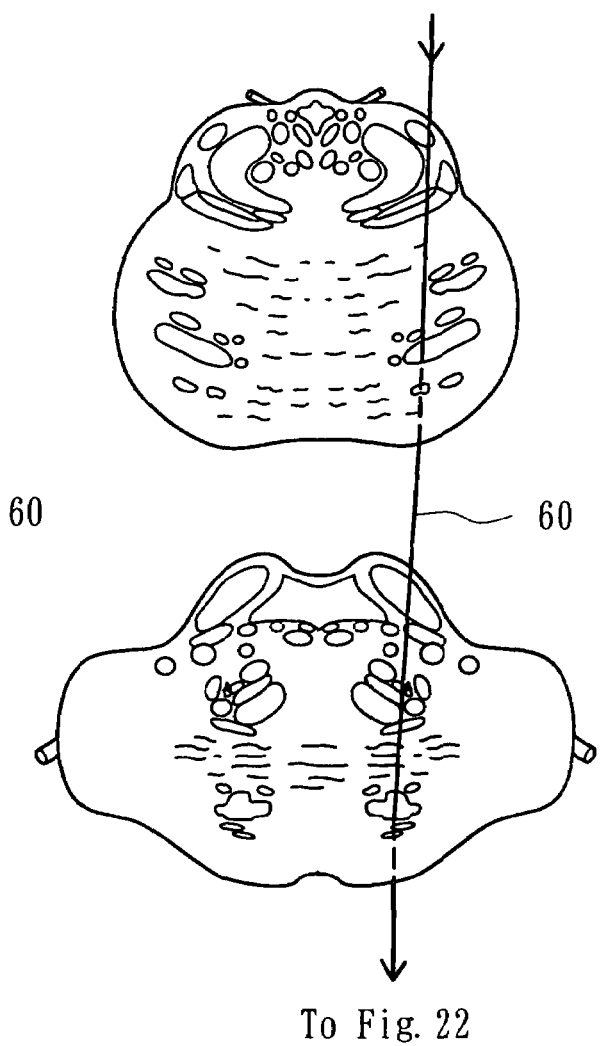
60
60
To Fig. 21
To Fig. 22

From Fig. 21

From Fig. 22

From Fig. 23

From Fig. 24

| Articulation | Movement | Depression of muscle force | Name of muscle | Electromyogram aberrance |
|---|---|---|---|---|
| Shoulder joint | Flexion | No | Deltoideus muscle | No |
| | | | Coracobrachialis muscle | No |
| | Stretch | No | Teres major muscle | No |
| | | | Broadest muscle of back | No |
| | Excycloduction | No | Teres minor muscle | No |
| Elbow joint | Stretch | No | Triceps muscle of arm | No |
| | | | Musculi anconeus | No |
| | Flexion | Yes | Biceps muscle of arm | No |
| | | | Brachial muscle | No |
| | | | Musculi brachioradialis | Yes |
| Antebrachium | Supination | Yes | Antebrachium musculi spinator | Yes |
| Hand joint | Flexion | No | Musculi flexor carpi radialis | No |
| | | | Musculi flexor carpi ulnalis | No |
| | Stretch | Yes | Musculi extensor carpi radialis longus | Yes |
| | | | Musculi extensor carpi radialis brevis | Yes |
| | | | Musculi extensor carpi ulnaris | Yes |
| . | . | . | . | . |
| . | . | . | . | . |
| . | . | . | . | . |

Columns: 71, 72, 73, 70, 74, 75

SYSTEM FOR TOPICAL NERVE DIAGNOSIS AND NEUROANATOMICAL STUDY

FIELD OF THE INVENTION

The present invention relates to a system for topical nerve diagnosis and neuroanatomical study with the use of a computer.

BACKGROUND ART

In a conventional topical nerve diagnosis, a medical physician presumes associated nerve pathways which will cause symptoms of abnormality in neural functions such as motor paralysis, perception disorder such as numbness, accommodation disorder in diaphoresis or blood pressure, abnormality in balance or muscle tone, and abnormality in allophasis or tendon reflex based on a neural finding with respect to a patient, and decides an associated lesion which causes the symptom.

In this case, the medical physician must decide the associated lesion by using his (or her) own knowledge of neuroanatomy while imaging associated nerve pathways related to the abnormal neural findings as well as positional relations of those associated nerve pathways. However, knowledge of neuroanatomy required for such diagnosis is an enormous amount, so that it is difficult to memorize perfectly the contents of neuroanatomy.

Hence, in a conventional topical nerve diagnosis, an associated lesion has been decided on the basis of physician's experience and gut feel, so that there was a case where an incorrect diagnosis was made.

Furthermore, medical students are required in learning of neuroanatomy to read thoroughly books of neuroanatomy, to understand details of nerve pathway diagrams, besides details of nerve pathway cut surface diagrams in regions of cerebrum, brainstem, spinal cord and the like, and to memorize correctly them. However, nerve pathway diagrams and nerve pathway cut surface diagrams are very complicated, and an amount of information derived therefrom and to be memorized is enormous amount. Accordingly, it was very difficult in general to memorize correctly such information. (For example, see "SHINKEI SHINDANGAKU NYUMON (Principles of Neurologic Diagnosis)" authored by Erwin B. Montogomery, Michael Wall, and Victor W.

Henderson; translated by supervision of Shunsaku Hirai; published from Medical Science International; May 1987; and "RINSHOH NO TAMENO SHINKEIKINOU KAIBO-HGAKU (Neurological Function Anatomy for Clinic)" authored by Fumio Gotoh and Takahiro Amano; published from Chuhgai Igaku-sha; 1996)

DISCLOSURE OF THE INVENTION

It is an object of the present invention to provide a system enabling medical physicians to rapidly and correctly make a topical nerve diagnosis without relying upon his (or her) own experience and gut feel.

It is another object of the present invention to provide a system enabling medical students to easily understand nerve pathway diagrams and nerve cut surface diagrams in neuroanatomy, and memorize efficiently the contents thereof.

In order to achieve those objects, the present invention provides a topical nerve diagnostic system with the use of a computer, comprising a first data recording part storing data of a whole nerve pathway diagram; a first input part for receiving input data of neural findings; a first data extraction part extracting data for drawing associated nerve pathways related to abnormal neural findings from the data stored in the first data recording part according to neural finding data inputted through the first input part; a display; a whole nerve pathway indication part displaying a whole nerve pathway diagram on said display based on the data stored in the first data recording part; an associated nerve pathway indication part drawing associated nerve pathways in the whole nerve pathway diagram displayed on the display based on the data extracted by the first data extraction part; and an associated lesion estimation and indication part calculating a position of each of associated lesions and indicating the associated lesions in the whole nerve pathway diagram based on the associated nerve pathways drew on the display by the associated nerve pathway indication part.

According to a preferred embodiment of the present invention, the data stored in the first data recording part contains data of names of nerve nuclei and positions thereof in the whole nerve pathway diagram, data of connection relations of the nerve nuclei, and data of curves and straight lines representing nerve fascicles which connect the nerve nuclei with each other.

According to another preferred embodiment of the present invention, the first data extraction part extracts from the first data recording part, data of names of associated nerve nuclei and positions thereof in the whole nerve pathway diagram, data of connection relations of the associated nerve nuclei, and data of curves and straight lines representing nerve fascicles which connect the associated nerve nuclei with each other when a neural finding is an abnormal neural finding.

According to a further preferred embodiment of the present invention, the associated lesion estimation and indication part detects a region where associated nerve pathways displayed on the display intersect with each other and a region where associated nerve pathways approach each other at closest distance, and presumes the detected regions to be associated lesions so as to display the associated lesion in the whole nerve pathway diagram on the display.

According to a still further preferred embodiment of the present invention, the topical nerve diagnostic system includes a second data recording part storing cut surface data of specified regions of the whole nerve pathway diagram; a second input part for receiving input data of selection as to a cut surface of which region is to be indicated in the whole nerve pathway diagram displayed on said display; a second data extraction part extracting data for drawing associated nerve pathways related to abnormal neural findings in a cut surface of a specified region from the data stored in the second data recording part according to both the data inputted through the second input part and the data inputted through the first input part; a nerve pathway cut surface indication part extracting associated cut surface data from the data stored in the second data recording part according to the data inputted through said second input part so as to display the associated cut surface; a second associated nerve pathway indication part drawing associated nerve pathways in the nerve pathway cut surface displayed by the nerve pathway cut surface indication part based on the data extracted by the second data extraction part; and a second associated lesion estimation and indication part calculating a position of each of associated lesions in the associated cut surface based on the associated nerve pathways displayed on the display by the second associated nerve pathway indication part so as to display the associated lesions in the associated cut surface.

According to an yet further preferred embodiment of the present invention, the data stored in the second data recording part contains data of names of nerve nuclei and positions thereof in the cut surface, data of connection relations of nerve nuclei, and data of curves and straight lines representing nerve fascicles which connect the associated nerve nuclei with each other in the every cut surfaces.

According to a still further preferred embodiment of the present invention, the second data extraction part extracts from said second data recording part, data of names of associated nerve nuclei and positions thereof in the cut surface, data of connection relations of the associated nerve nuclei, and data of curves and straight lines representing nerve fascicles which connect the associated nerve nuclei with each other second data recording part when a neural finding is an abnormal neural finding.

According to a further preferred embodiment of the present invention, the second associated lesion estimation and indication part detects a region where associated nerve pathways displayed on the display intersect with each other and a region where associated nerve pathways approach each other at closest distance, and presumes the detected regions to be associated lesions so as to display the associated lesions in the cut surface.

According to an yet further preferred embodiment of the present invention, the topical nerve diagnostic system includes a screen page switchover part switching over a screen page between a screen page of the whole nerve pathway diagram and a screen page of a cut surface of a specified region of the whole nerve pathway diagram.

According to a still further preferred embodiment of the present invention, the neural findings include oculomotor restriction, inferior oculomotor restriction, jaw reflex acceleration, impaired facial tactual sensation, impaired facial pain/temperature sensation, corneal areflexia, exterior oculomotor restriction no, upper facial paralysis, lower facial paralysis, impaired taste, lowered pharyngeal reflex/swallowing difficulty, impaired pharyngeal sound dysphemia, lingual muscle paralysis/impaired lingual sound dysphemia, sternocleidomastoid paralysis, impaired upper limb pain/temperature sensation, impaired upper limb deep sensation, upper limb motor paralysis, superior limb tendon reflex, impaired trunk pain/temperature sensation, impaired trunk deep sensation, level of impaired trunk deep sensation, impaired lower limb pain/temperature sensation, inferior bathyesthesia disorder, lower limb motor paralysis, inferior limb tendon reflex, and Babinski reflex.

According to an yet further preferred embodiment of the present invention, the data stored in the first data recording part contains data of names of spinal roots, muscles and skin areas and positions thereof in the whole nerve pathway diagram, data of connection relations of the spinal roots and the muscles, and data of curves and straight lines representing nerve fascicles which connect the spinal roots with the muscles as well as data of connection relations of the spinal roots and the skin areas, and curves and straight lines which connect the spinal roots with the skin areas.

According to a further preferred embodiment of the present invention, the first data extraction part extracts from the first data recording part data of names of associated spinal roots, associated muscle and associated skin areas and positions thereof in the whole nerve pathway diagram, data of connection relations of the associated spinal roots and the associated muscles, and data of curves and straight lines representing nerve fascicles which connect the associated spinal roots with the associated skin areas as well as data of connection relations of the associated spinal roots and the associated skin areas, and data of curves and straight lines which connect the associated spinal roots with the associated skin areas when a neural finding is an abnormal neural finding.

According to a still further preferred embodiment of the present invention, the associated lesion estimation and indication part detects a region where associated nerve pathways displayed on the display overlap with each other at the highest degree, and presume the detected region to be an associated lesion so as to display the associated lesion in the whole nerve pathway diagram on the display.

According to an yet further preferred embodiment of the present invention, the topical nerve diagnostic system includes a third associated lesion estimation and indication part removing an associated nerve pathway part corresponding to nerve fascicles which connect a muscle or a skin area which is related to data of normal findings with the associated spinal roots from the associated nerve pathways drew in the whole nerve pathway diagram on the display by said associated lesion estimation and indication part in the case when data of an abnormal neural finding of the muscles or the skin areas which are related to the associated nerve pathways is inputted through said first input part.

According to a still further preferred embodiment of the present invention, the neural findings include findings with respect to muscle strength related to movement of joints and perception disorder of skin areas.

In order to achieve the above-mentioned objects, the present invention provides a neuroanatomy learning system with the use of a computer, characterized by having a second data recording part for recording cut surface data in at least one region of cerebrum and mesencephalon, at least one region of pons, at least one region of medulla oblongata, and at least one region of spinal cord, respectively, in a whole pathway diagram; a display; a nerve pathway cut surface indication part for displaying cut surfaces of at least one region of the cerebrum and the mesencephalon, at least one region of the pons, at least one region of the medulla oblongata, at least one region of the medulla oblongata, and at least one region of the spinal cord, respectively, in this order based on the data stored in the second data recording part; a nerve pathway selection data input part for receiving selection data input of nerve pathways to be displayed on the display; a nerve pathway data extraction part for extracting data for drawing relevant nerve pathways from the data stored in the second data recording part based on the data received by the nerve pathway selection data input part in every nerve pathway cut surfaces; a nerve pathway indication part for displaying relevant nerve pathways in a nerve pathway cut surface displayed by the nerve pathway cut surface indication part based on the data extracted by the nerve pathway data extraction part; a nerve pathway cut surface selection data input part for receiving selection data input for a nerve pathway cut surface which is intended to individually display among the nerve pathway cut surfaces displayed on the display by means of the nerve pathway cut surface indication part; an individual nerve pathway cut surface data extraction part for extracting data for drawing a relevant nerve pathway cut surface from the data stored in the second data recording part based on the data received by the nerve pathway cut surface selection data input part; an individual nerve pathway cut surface indication part for displaying a relevant nerve pathway cut surface on the display based on the data extracted by the individual nerve pathway cut surface data extraction part; and a nerve pathway-nerve nucleus name indication part for displaying a name of a nerve pathway or a nerve nucleus which is selected in the nerve pathway cut surface displayed on the display by means of the individual nerve pathway cut surface indication part.

According to a preferred embodiment of the present invention, the data stored in the second data recording part contains data of relevant names and positions of nerve nuclei in the cut surfaces, relevant connection relations in the nerve nuclei, and curves or straight lines representing nerve fascicles for connecting relevant nerve nuclei with each other, and names of relevant nerve pathway and positions in the cut surfaces in every cut surfaces.

According to another preferred embodiment of the present invention, at least one region of the mesencephalon consists of the upper part of the mesencephalon and the lower part of the mesencephalon, at least one region of the pons consists of the upper, the middle, and the lower parts of the pons, at least one region of the medulla oblongata consists of the upper part, the upper-middle part, the middle, the middle-lower part, and the lower part of the medulla oblongata, and at least one region of the spinal cord consists of a cervical segment, a thoracic segment, and a lumbar segment.

BRIEF DESCRIPTION OF THE DRAWINGS

FIG. 2 is a diagram showing an example of a screen page for inputting neural finding data.

FIG. 3 is a diagram showing an example of a screen page for inputting neural finding data.

FIG. 4 is a diagram showing an example of a screen page for inputting neural finding data.

FIG. 5 is a diagram showing an example of a screen page for inputting neural finding data.

FIG. 6 is a diagram showing an example of a screen page for inputting neural finding data.

FIG. 7 is a diagram showing an example of a screen page for inputting neural finding data.

FIG. 8 is a diagram showing an example of a screen page for inputting neural finding data.

FIG. 20 is a view showing a part of a series of nerve pathway cut surfaces with a nerve pathway indicated therein.

FIG. 21 is a view showing a part of a series of nerve pathway cut surfaces with a nerve pathway indicated therein.

FIG. 27 is a diagram showing an example of a screen page for inputting neural finding data.

BEST MODE FOR CARRYING OUT THE INVENTION

Figure 1:
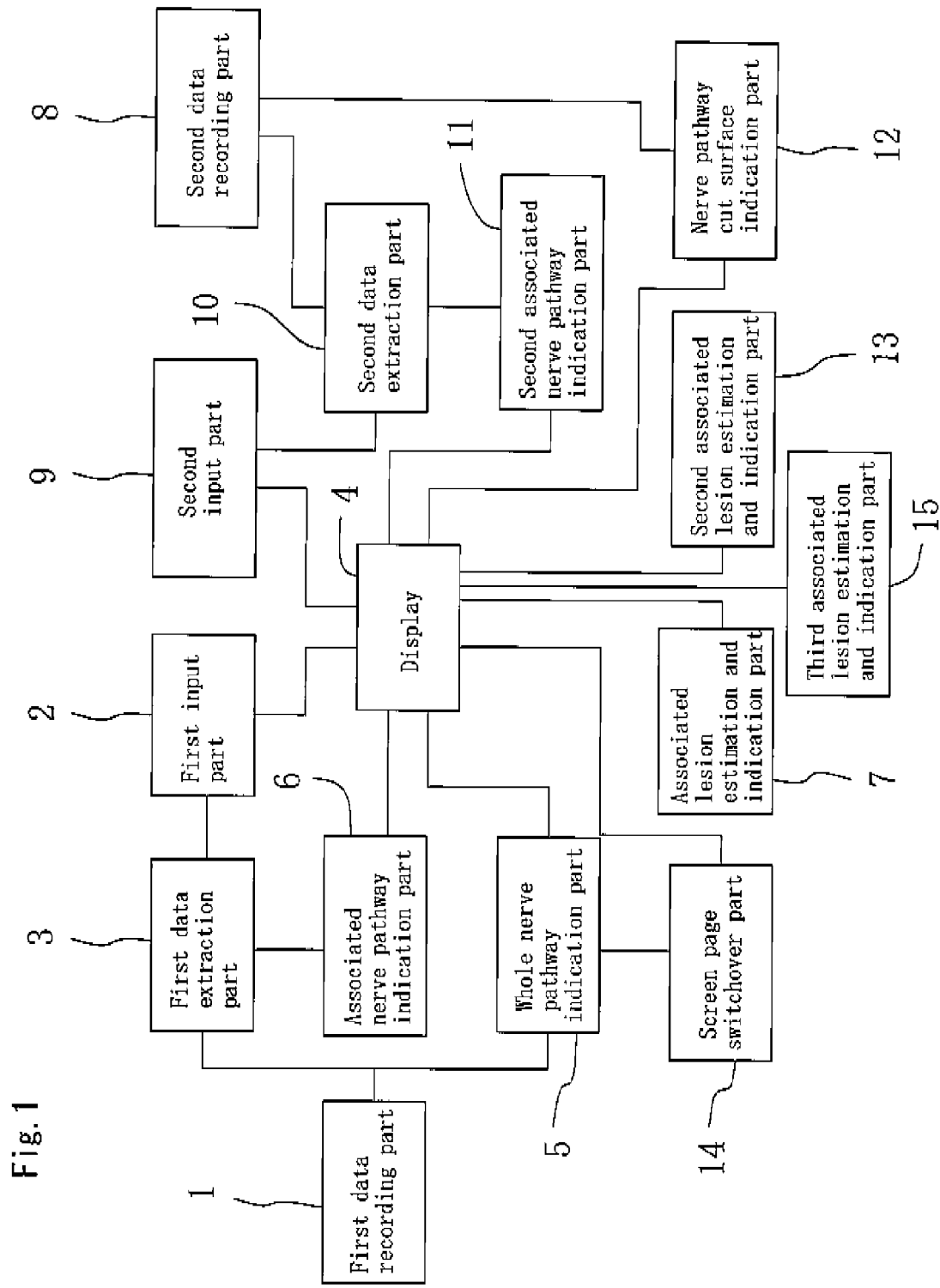
FIG. 1 is a block diagram of a topical nerve diagnostic system according to an embodiment of the present invention.

In the following, preferred embodiments of the present invention will be described by referring to the accompanying drawings. FIG. 1 is a block diagram of a topical nerve diagnostic system according to an embodiment of the present invention. The topical nerve diagnostic system utilizes a computer and operates independently in two modes of a central topical nerve diagnosis mode and a peripheral topical nerve diagnosis mode.

Referring to FIG. 1, the topical nerve diagnostic system involves a first data recording part 1 storing data of a whole nerve pathway diagram. The data stored in the first data recording part 1 contains data of names of nerve nuclei and positions thereof in the whole nerve pathway diagram, data of connection relations of the nerve nuclei, and data of curves and straight lines representing nerve fascicles which connect nerve nuclei with each other for the purpose of diagnosis of central neural system, while data of names of spinal roots, muscles and skin area and positions thereof in the whole nerve pathway diagram, data of connection relations of the spinal roots and the muscles, and data of curves and straight lines representing nerve fascicles which connect the spinal roots with the muscles as well as data of connection relations of the spinal roots and the skin areas, and data of curves and straight lines representing nerve fascicles which connect the spinal roots with the skin areas for the purpose of diagnosis of peripheral neural system.

Figure 29:
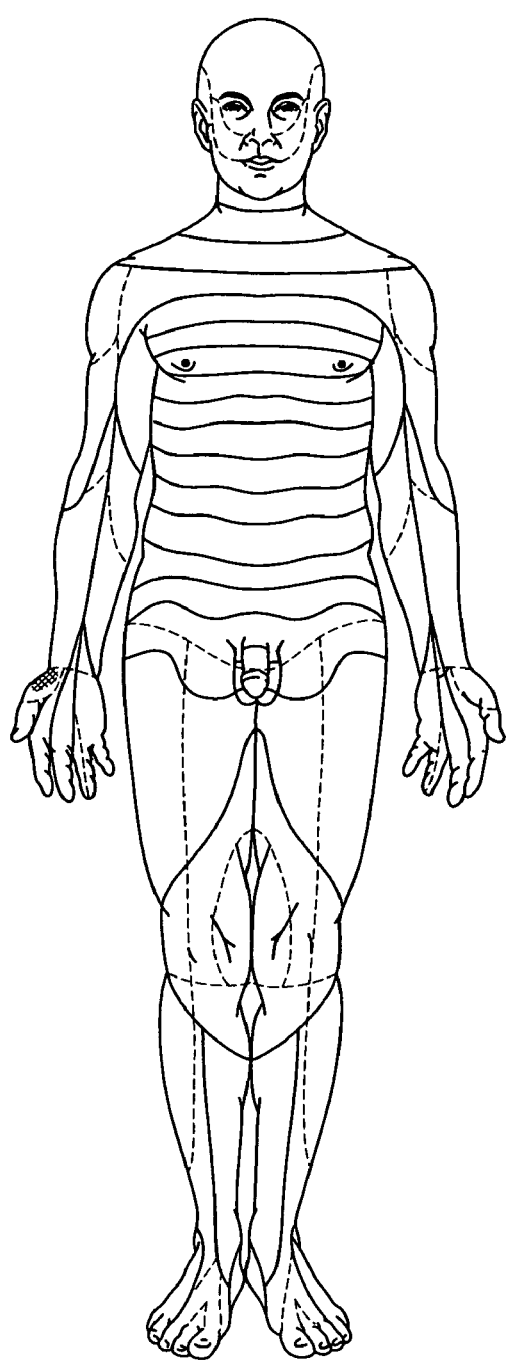
FIG. 29 is a view showing segments of a skin area.

In the present embodiment, the names of the skin areas and the positions thereof in the whole nerve pathway diagram are previously determined by superposing a spinal rooting sense dominant diagram to a peripheral neural sense dominant diagram as shown in FIG. 29.

The system of the present invention is further provided with a first input part 2 for receiving input data of neural findings, a first data extraction part 3 extracting data for drawing an associated nerve pathway related to abnormal neural findings from the data stored in the first data recording part 1 on the basis of the data inputted through the first input part 2, and a display 4.

The first input part 2 displays the data input screen page on the display 4 as shown in FIG. 2 in a central topical nerve diagnosis mode. Referring to FIG. 2, the data input screen page has a form of a table 20 containing a neural finding indication columns 21 vertically laid out, and data input columns 22 and 23 for inputting data as to whether a neural finding is a normal finding or an abnormal finding ("no" is input in case of a normal finding, while "yes" is input in case of an abnormal finding in the present embodiment). The data input columns 22 and 23 consist of the columns 22 for input of data relating to the left side of a human body and the columns 23 for input of data relating to the right side of the human body.

In this case, the neural findings include oculomotor restriction, inferior oculomotor restriction, jaw reflex acceleration, impaired facial tactual sensation, impaired facial pain/temperature sensation, corneal areflexia, exterior oculomotor restriction no, upper facial paralysis, lower facial paralysis, impaired taste, lowered pharyngeal reflex/swallowing difficulty, impaired pharyngeal sound dysphemia, lingual muscle paralysis/impaired lingual sound dysphemia, sternocleidomastoid paralysis, impaired upper limb pain/temperature sensation, impaired upper limb deep sensation, upper limb motor paralysis, upper limb tendon reflex acceleration no, impaired trunk pain/temperature sensation, impaired trunk deep sensation, level of impaired trunk deep sensation, impaired lower limb pain/temperature sensation, impaired lower limb deep sensation, lower limb motor paralysis, lower limb tendon reflex acceleration no, and Babinski reflex. However, neural findings are not limited to those specified in the present embodiment, but the other neural findings may be added.

Figure 28:
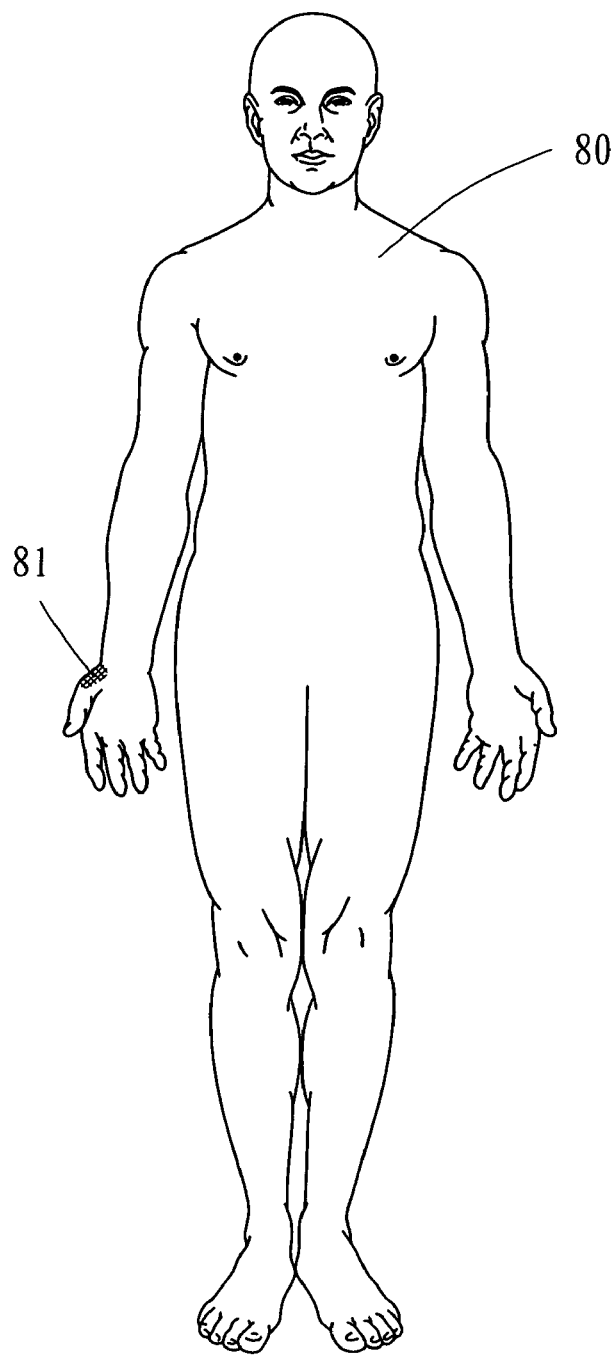
FIG. 28 is a diagram showing an example of a screen page for inputting neural finding data.

Furthermore, the first input part 2 displays data input screen pages as shown in FIGS. 27 and 28 on the display 4 in the peripheral topical nerve diagnosis mode. In this case, the data input screen page shown in FIG. 27 is adapted for inputting neural findings relating to motor nerve system, while the data input screen page shown in FIG. 28 is adapted for inputting neural findings relating to sensory nerve system.

Referring to FIG. 27, the data input screen page has a form of a table 70 containing a glenoid name indication columns 71 vertically laid out, data input columns 72 and 73 for inputting data as to whether a neural finding is a normal finding or an abnormal finding with respect to respective articular movements (such as bending and stretching), more specifically, presence of decrease in muscle strength in bending, stretching and the like movements as a result of empty-handed muscle strength test, muscle name indication columns 74 in which muscle names relating to movements of respective articulations are indicated, and data input columns 75 for inputting data as to whether the muscles have abnormality or not. Although the data as to whether the muscles have abnormality or not can be acquired by means of a variety of well-known manners, they are obtained by, for example, checking abnormality in electromyograms of respective muscles in the present embodiment. Accordingly, the data input columns 75 have the form of an electromyogram finding data input columns 75 in the table 70 of FIG. 27.

Next, referring to FIG. 28, the data input screen page is in the form of a plan view of human body 80. The plan view of human body 80 is united into a predetermined number of regions (skin areas) as shown in FIG. 29. In this respect, it is arranged in such that when a region where a sensorial disorder arises is pointed out by means of, for example, an appropriate pointing device such as a mouse on the plan view of human body 80, data of a name of the corresponding skin area and its position in the whole nerve pathway diagram are input, so that finding data as to the sensorial disorder of the skin areas are input.

The first data extraction part 3 extracts from the first data recording part 1, data of names of associated nerve nuclei and positions thereof in the whole nerve pathway diagram, data of connection relations of the associated nerve nuclei, and data of curves and straight lines representing nerve fascicles which connect the associated nerve nuclei with each other in a central topical nerve diagnosis mode. Furthermore, the first data extraction part 3 extracts from the first data recording part 1, data of names of associated spinal roots, associated muscle and associated skin areas and positions thereof in the whole nerve pathway diagram, data of connection relations of the associated spinal roots and the associated muscles, and data of curves and straight lines representing nerve fascicles which connect the associated spinal roots with the associated skins as well as data of connection relations of the associated spinal roots and the associated skin areas, and data of curves and straight lines which connect the associated respective spinal roots with the associated skin areas in a peripheral topical nerve diagnosis mode.

Furthermore, the first data extraction part 3 extracts from the first data recording part 1, data of names of associated spinal roots, associated muscle and associated skin area and positions thereof in the whole nerve pathway diagram, data of connection relations of the associated spinal roots and the associated muscles, and data of curves and straight lines representing nerve fascicles which connect the associated spinal roots with the associated skins as well as data of connection relations of the associated spinal roots and the associated skin areas, and data of curves and straight lines which connect the associated spinal roots with the associated skin areas in a peripheral topical nerve diagnosis mode.

The system of the present invention is further provided with a whole nerve pathway indication part 5 displaying the whole nerve pathway diagram on the display 4 based on the data stored in the first data recording part 1, and an associated nerve pathway indication part 6 drawing associated nerve pathways in the whole nerve pathway diagram displayed on the display 4 by the whole nerve pathway indication part 5.

Figure 9:
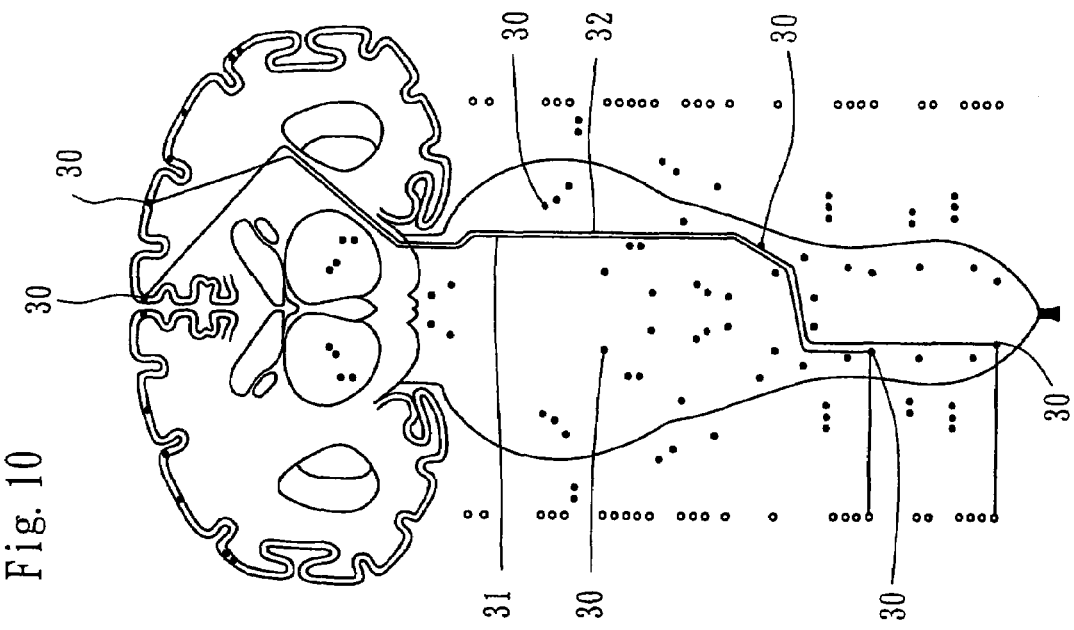
FIG. 9 is a view showing an example of a whole nerve pathway diagram with associated nerve pathways indicated therein.

FIG. 9 shows the whole nerve pathway diagram displayed on the display 4, and an example of associated nerve pathways in the central topical nerve diagnosis mode. In FIG. 9, only an outline of the whole nerve pathway diagram, nerve nuclei, and associated nerve pathways are shown for the clarity. In FIG. 9, the reference numeral 30 designates a nerve nucleus, and the reference numeral 31 designates an associated nerve pathway displayed by the associated nerve pathway indication part 6.

It is preferred that the whole nerve pathway diagram and each of the associated nerve pathways are displayed with different colors one another on the display 4. As a result, it becomes possible to clearly recognize visually the whole nerve pathway diagram and the respective associated nerve pathways.

The system of the present invention further comprises an associated lesion estimation and indication part 7 which calculates a position of each of associated lesions and indicating the associated lesions in the whole nerve pathway diagram on the basis of the associated nerve pathways drew on the display 4 by the associated nerve pathway indication part 6.

The associated lesion estimation and indication part 7 detects a region where associated nerve pathways displayed on the display 4 intersect with each other and a region where associated nerve pathways approach each other at closest distance, and presumes the detected regions to be an associated lesions so as to display the associated lesions in the whole nerve pathway diagram of the display 4 in the central topical nerve diagnosis mode. Moreover, the associated lesion estimation and indication part 7 detects a region where associated nerve pathways displayed on the display 4 overlap with each other at the highest degree, and presume the detected region to be an associated lesion so as to display the associated lesion in the whole nerve pathway diagram of the display 4 in the peripheral topical nerve diagnosis mode. It is preferred that associated lesions are displayed on the display 4 with a different color from those of the whole nerve pathway diagram and the associated nerve pathways.

Furthermore, the system of the present invention includes a third associated lesion estimation and indication part 15 which removes an associated nerve pathway part corresponding to nerve fascicles connecting a muscle which is related to data of normal finding inputted through the data input screen page shown in FIG. 27 with the associated spinal roots from the associated nerve pathways drew in the whole nerve pathway diagram on the display 4 by the associated lesion estimation and indication part 7 when data of an abnormal finding is inputted through the first input part 2 with respect to electromyogram of muscles related to the associated nerve pathways in a peripheral topical nerve diagnosis mode.

The system of the present invention further includes a second data recording part 8 storing data of cut surfaces of specified regions in the whole nerve pathway diagram. The data stored in the second data recording part 8 contains data of names of nerve nuclei and positions thereof in the cut surfaces, data of relevant connection relations of the nerve nuclei, and data of curves and straight lines representing nerve fascicles which connect nerve nuclei with each other in every cut surfaces.

Moreover, the system of the present invention is provided with a second input part 9 for receiving input data of selection as to a cut surface of which region in the whole nerve pathway diagram is to be indicated on the display 4, and a second part data extraction part 10 extracting data for drawing associated nerve pathways related to abnormal neural findings in a cut surface of a specified region from the data stored in the second data recording part 8 on the basis of the data inputted through the second input part 9 and the data inputted through the first input part.

The second data extraction part 10 extracts from the data of the cut surfaces stored in the second data recording part 8, data of names of associated nerve nuclei and positions thereof in the cut surfaces, data of connection relations of the associated nerve nuclei, and data of curves and straight lines representing nerve fascicles which connect nerve nuclei with each other.

The system of the present invention is further provided with a nerve pathway cut surface indication part 12 which extracts relevant data of cut surfaces from the data stored in the second data recording part 8 based on the data inputted through the second input part 9 to display relevant cut surfaces, and a second associated nerve pathway indication part 11 which draws associated nerve pathways in a nerve pathway cut surface displayed by the nerve pathway cut surface indication part 12 based on the data extracted by the second data extraction part 10.

In this case, it is preferred that nerve pathway cut surfaces and each of associated nerve pathways are displayed with different colors on the display 4, whereby it becomes possible to clearly recognize visually the whole nerve pathway diagram and respective associated nerve pathways.

The system of the present invention includes a second associated lesion estimation and indication part 13 calculating a position of each of an associated lesions in cut surfaces on the basis of an associated nerve pathways drew on the display 4 by the second associated nerve pathway indication part 11 so as to display the associated lesions in the cut surface.

The second associated lesion estimation and indication part 13 detects a region where associated nerve pathways displayed on the display 4 intersect with each other and a region where associated nerve pathways approach each other at closest distance, and presume the detected regions to be an associated lesions so as to display the associated lesions in the cut surface. In this case, it is preferred that such associated lesions are displayed on the display 4 with a different color from those of the nerve pathway cut surface and the associated nerve pathways.

Moreover, the system of the present invention is provided with a screen page switchover part 14 for switching over a screen page between a screen page of a whole nerve pathway diagram and a screen page of a cut surface in a specified region of the whole nerve pathway diagram in a central topical nerve diagnosis mode.

In the following, the operation of the topical nerve diagnostic system will be described. First, a case where the system according to the present invention is operated in a central topical nerve diagnosis mode will be described.

For instance, it is supposed that there are observed (1) right side paralysis (paralysis of right limbs), (2) left peripheral facial paralysis, (3) abduction disorder of left eye (paralysis of abducent nerve), (4) sthenia of tendon reflex in right limbs, and (5) Babinski reflex as neural findings with respect to a patient.

Figure 10:
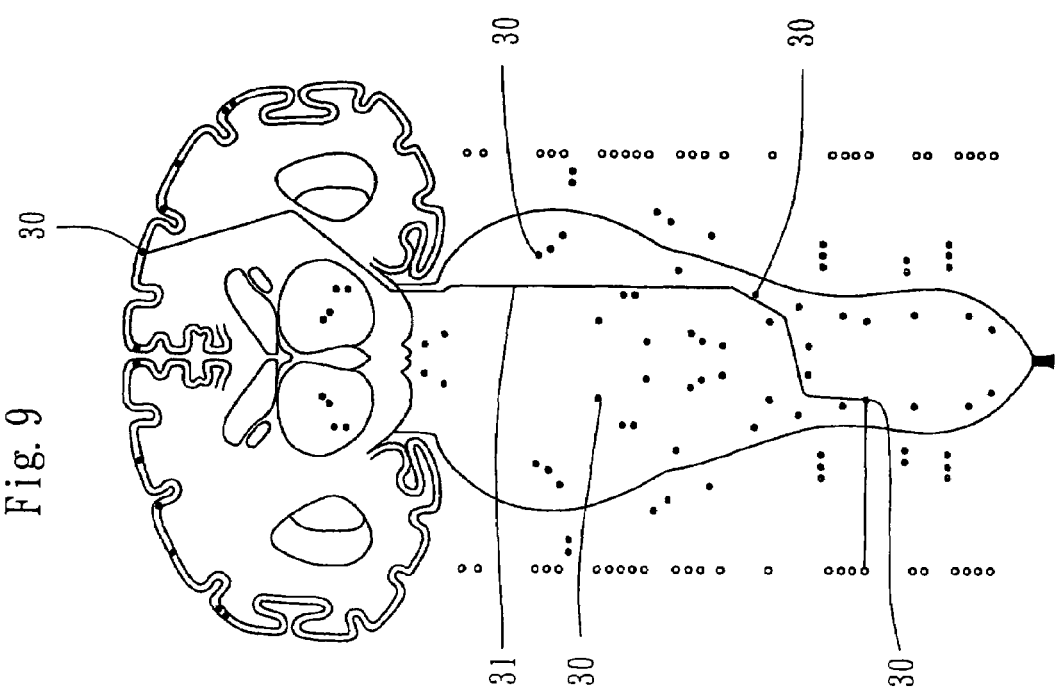
FIG. 10 is a view showing an example of a whole nerve pathway diagram with associated nerve pathways indicated therein.

In this case, "yes" is input to a right side data input column in a neural finding "upper limb motor paralysis" as shown in FIG. 2 in a data input screen page displayed on the display 4. At this moment, a screen page shown in FIG. 9 is displayed on the display 4, and the associated nerve pathway 31 relating to an abnormal finding of "upper limb motor paralysis" on the right side of human body is displayed in the whole nerve pathway diagram of the display 4. Next, "yes" is input to a right side data input column in a neural finding "lower limb motor paralysis" as shown in FIG. 3 in a data input screen page. At this moment, a screen page shown in FIG. 10 is displayed on the display 4, and the associated nerve pathway 32 relating to an abnormal finding of "lower limb motor paralysis" on the right side of human body is additionally displayed in the whole nerve pathway diagram.

Figure 11:
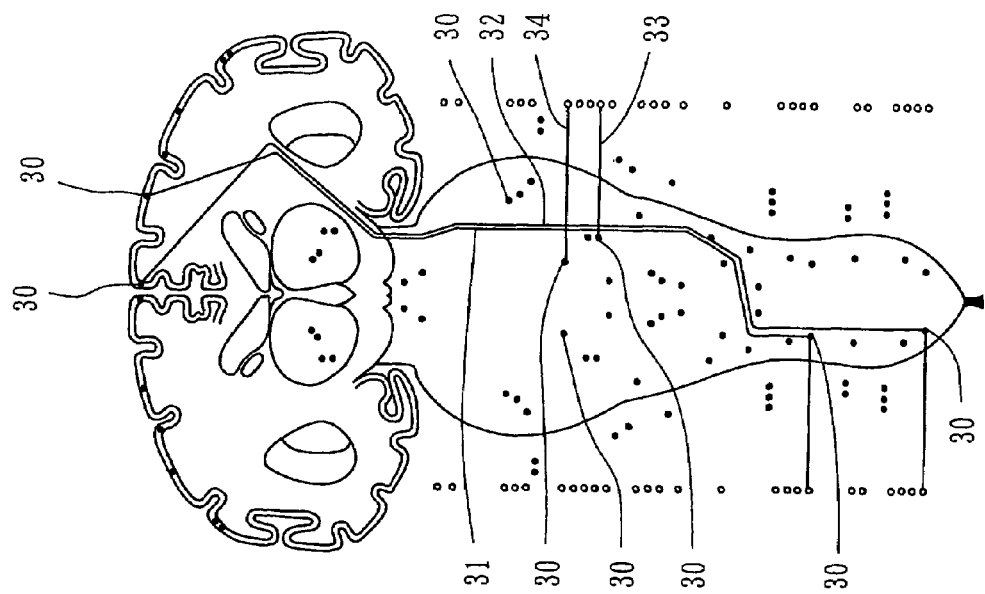
FIG. 11 is a view showing an example of a whole nerve pathway diagram with associated nerve pathways indicated therein.
Figure 12:
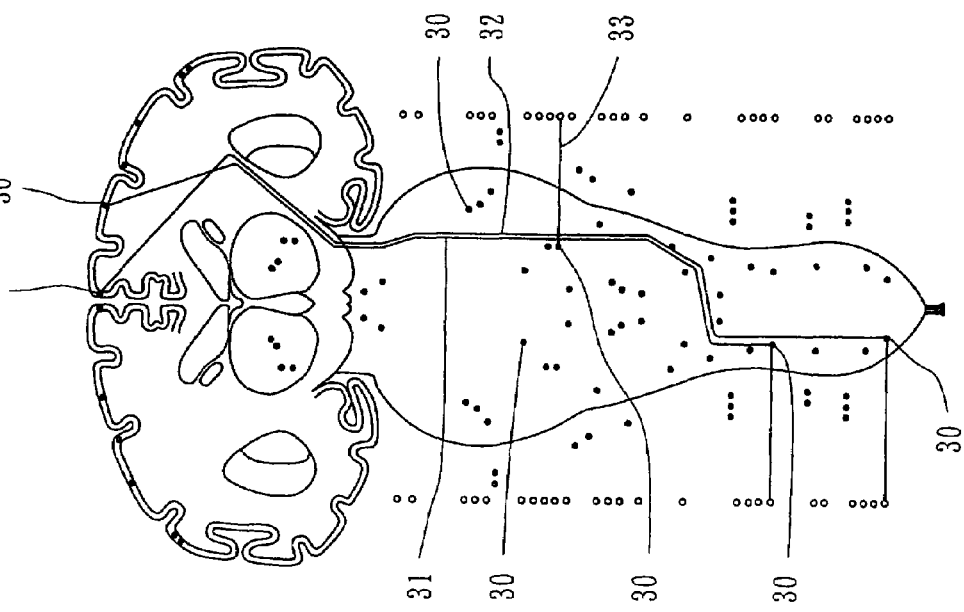
FIG. 12 is a view showing an example of a whole nerve pathway diagram with associated nerve pathways indicated therein.

Then, "yes" is input to a right side data input column in a neural finding "upper facial paralysis" as shown in FIG. 4 in a data input screen page. At this moment, a screen page shown in FIG. 11 is displayed on the display 4, and the associated nerve pathway 33 relating to an abnormal finding of "upper facial paralysis" on the left side of human body is additionally displayed in the whole nerve pathway diagram. Next, "yes" is input to a left side data input column in a neural finding "exterior oculomotor restriction no" as shown in FIG. 5 in a data input screen page. At this moment, a screen page shown in FIG. 12 is displayed on the display 4, and the associated nerve pathway 34 relating to an abnormal finding of "exterior oculomotor restriction no" on the left side of human body is additionally displayed in the whole nerve pathway diagram.

Figure 13:
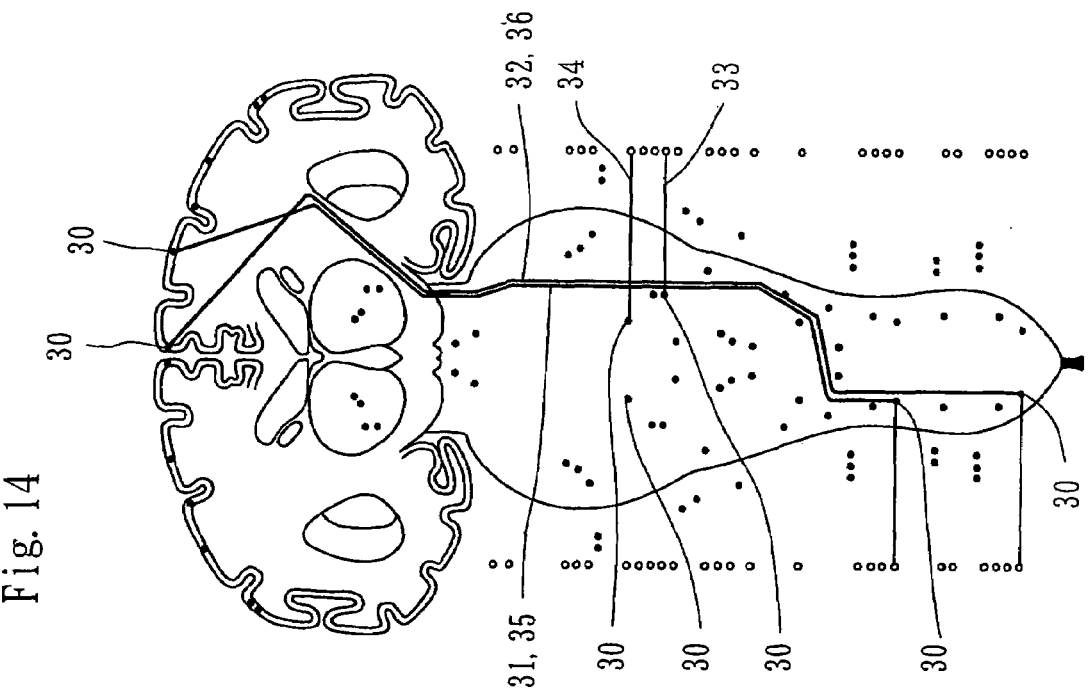
FIG. 13 is a view showing an example of a whole nerve pathway diagram with associated nerve pathways indicated therein.
Figure 14:
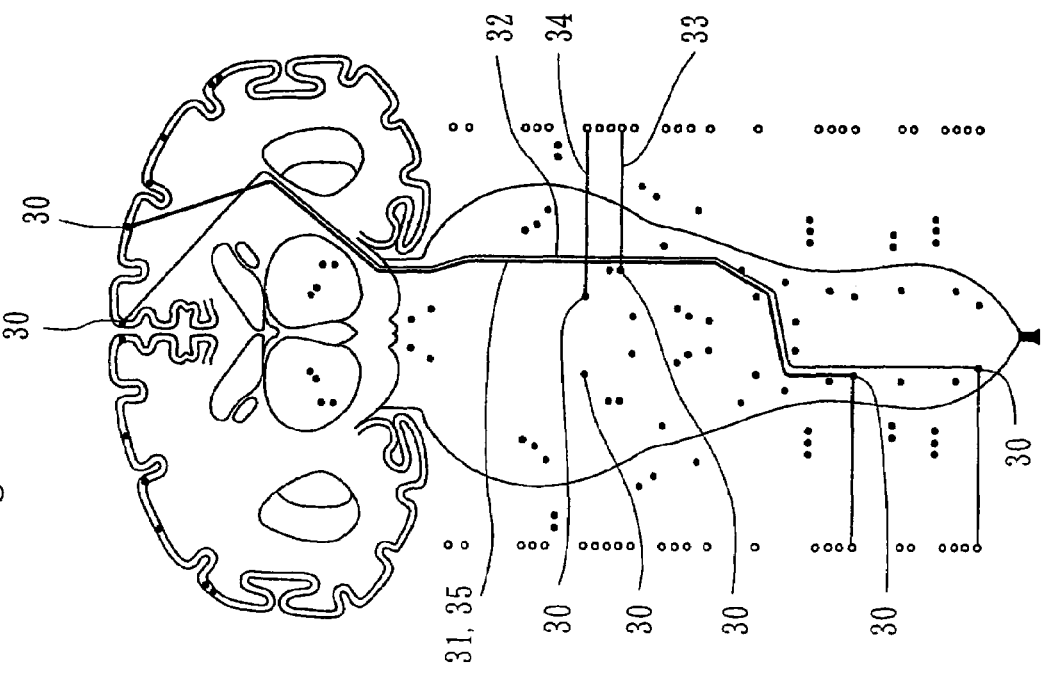
FIG. 14 is a view showing an example of a whole nerve pathway diagram with associated nerve pathways indicated therein.

Thereafter, "yes" is input to a right side data input column in a neural finding item "upper limb tendon reflex acceleration no" as shown in FIG. 6 in a data input screen page. At this moment, a screen page shown in FIG. 13 is displayed on the display 4, and the associated nerve pathway 35 relating to an abnormal finding of "upper limb tendon reflex acceleration no" on the right side of human body is additionally displayed in the whole nerve pathway diagram (a part of the associated nerve pathway 31 is thickened in this case). Then, "yes" is input to a right side data input column in a neural finding item "lower limb tendon reflex acceleration no" as shown in FIG. 7 in a data input screen page. At this moment, a screen page shown in FIG. 14 is displayed on the display 4, and the associated nerve pathway 36 relating to an abnormal finding of "lower limb tendon reflex acceleration no" on the right side of human body is additionally displayed in the whole nerve pathway diagram (a part of the associated nerve pathway 32 is thickened in this case). Moreover, "yes" is input to a right side data input column in a neural finding item "Babinski reflex" as shown in FIG. 8 in a data input screen page. At this moment, a screen page shown in FIG. 15 is displayed on the display 4, and the associated nerve pathway 37 relating to an abnormal finding of "Babinski reflex" on the right side of human body is additionally displayed in the whole nerve pathway diagram (a part of the associated nerve pathway 36 is thickened in this case).

When input of neural findings is completed, an associated lesion is presumed on the basis of the associated nerve pathways 32 to 37 (see FIG. 15) displayed on the display 4, and the result is displayed in the whole nerve pathway diagram. In the present embodiment, a substantially central area at the lower part of a left brainstem is detected as a region where the associated nerve pathways 32 to 37 approach each other at closest distance, so that the region is presumed to be an associated lesion, and it is displayed in the whole nerve pathway diagram. This is a brainstem abdominal side syndrome (Millard-Gubler syndrome) observed frequently as one of cerebral infarctions in brainstem. This affection is an important brainstem infarction syndrome as a so-called "alternating hemiplegia" in view of neurology, which exhibits such a situation where a side of paralysis in superior and inferior limbs is reverse with respect to that of facial paralysis, so that it is requested to understand complicated nerve pathways from the viewpoint of diagnosis.

Figure 15:
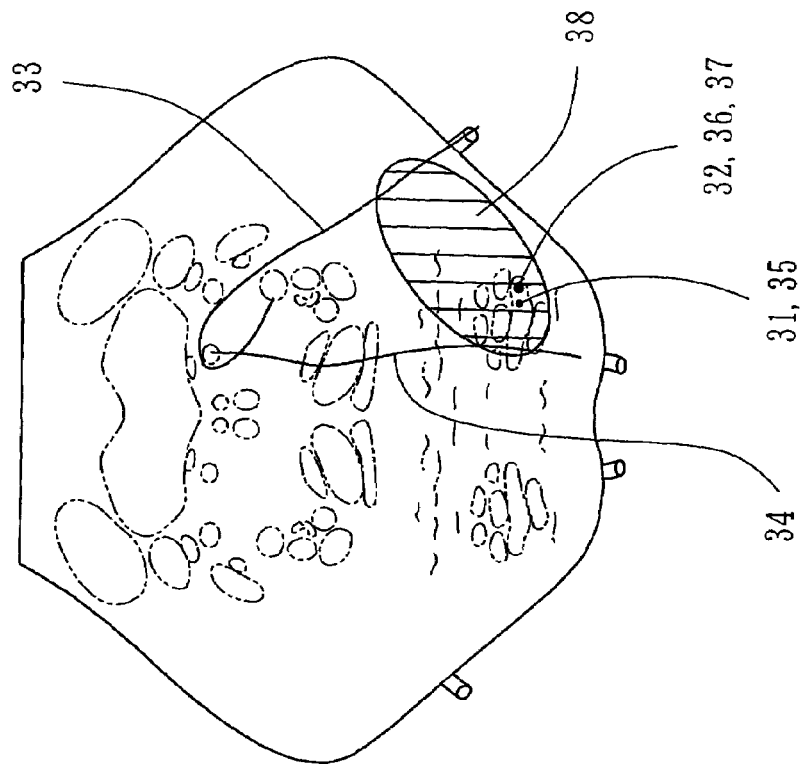
FIG. 15 is a view showing an example of a whole nerve pathway diagram with associated nerve pathways indicated therein.
Figure 16:
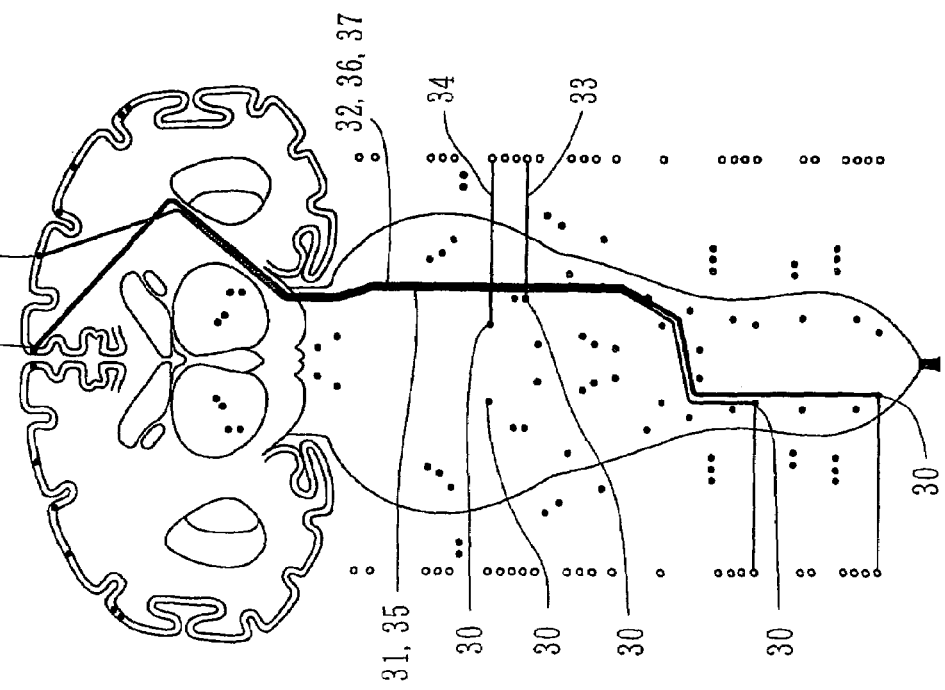
FIG. 16 is a view showing an example of a whole nerve pathway diagram with associated nerve pathways indicated therein.

In the whole nerve pathway diagram shown in FIG. 15, when a button for displaying a cut surface in a brainstem area is clicked, the cut surface of the brainstem area is displayed on the display 4, and an associated lesion 38 is also shown in the cut surface as shown in FIG. 16.

Thus, according to a topical nerve diagnostic system of the present invention, when only data of normal or abnormal findings are input, associated nerve pathways are displayed automatically together with a whole nerve pathway diagram, whereby associated lesions are automatically displayed with respect to a neural disease of a patient. Accordingly, a medical physician can give rapidly and correctly a diagnosis, which is not, made in accordance with physician's experience and gut feeling as in a conventional diagnosis.

There arises a rare case where associated lesions are displayed on the display 4 as a lump containing not only associated nerve pathways, but also normal nerve pathways which are not an associated nerve pathway. In this case, all the neural findings corresponding to the associated nerve pathways passing through the detected lesions are displayed on the display 4 based on the data stored in the first data recording part 1, the abnormal findings displayed are reviewed, required additional inspections are implemented, whereby operations for eliminating nerve pathways related to normal findings are repeatedly carried out so as to narrow down the number of the associated lesions, so that it becomes possible to presume the associated lesion at a higher precision.

In the following, the system according to the present invention will be described with respect to the case where the system is operated in a peripheral topical nerve diagnosis mode. For instance, it is supposed that a decrease in muscle strength is observed with respect to bending of an ancon articulation and stretching of a hand articulation as a result of empty-handed muscle strength test as a neural finding of a motor nerve system as to a patient, and a perception disorder is observed in the skin area 81 shown in FIG. 29 as a neural finding of a sensory nerve system.

In the above case, "yes" is input to a data input column of "decrease in muscle strength" of a finding "bending movement" as to "ancon articulation" and at the same time, "yes" is input to a data input column of "decrease in muscle strength" of a finding "stretching movement" as to "hand articulation". Furthermore, the skin area 81 is specified by a pointing device in the data input screen page in FIG. 28, and a name and a position are input in the skin area.

At this moment, a screen page shown in FIG. 29 is displayed on the display 4, and an associated nerve pathway 90 related to abnormal finding of a bending movement in an ancon articulation and abnormal finding of perception disorder in the skin area 81 are displayed in the whole nerve pathway diagram of the display 4. In FIG. 29, the reference numerals a to q designate muscles or skin areas relating to questioned abnormal findings wherein a represents deltoideus muscle, b represents teres minor muscle, c represents long head of triceps muscle of the arm, d represents lateral head of triceps muscle of the arm, e represents musculi anconeus, f represents musculi brachioradialis, g represents musculi extensor carpi radialis longus, h represents musculi extensor carpi radialis brevis, i represents musculi spinator, j represents musculi extensor carpi ulnaris, k represents musculi extensor digitorum, l represents musculi extensor digiti minimi, m represents musculi abductor pollicis longus, n represents musculi extensor pollicis longus, o represents musculi extensor pollicis brevis, p represents musculi extensor indicis, and q represents radial nerve skin perception branch. Furthermore, A and B designate spinal roots relating to questioned abnormal findings, respectively, and S designates spinal cord. In the circumstances, the muscles and skin areas a to q are connected with relevant spinal roots A and B through nerve fascicles, respectively.

When input of neural findings is completed with respect to a patient, an associated lesion is detected on the basis of the associated nerve pathway 90 displayed on the display 4, whereby the associated lesion is displayed in the whole nerve pathway diagram. In the present embodiment, an area extending from a skin area 91 to the musculi brachioradialis is detected as an area where associated nerve pathways overlap the most frequently with each other, so that it is presumed to be an associated lesion, and it is displayed in the whole nerve pathway diagram.

Figure 30:
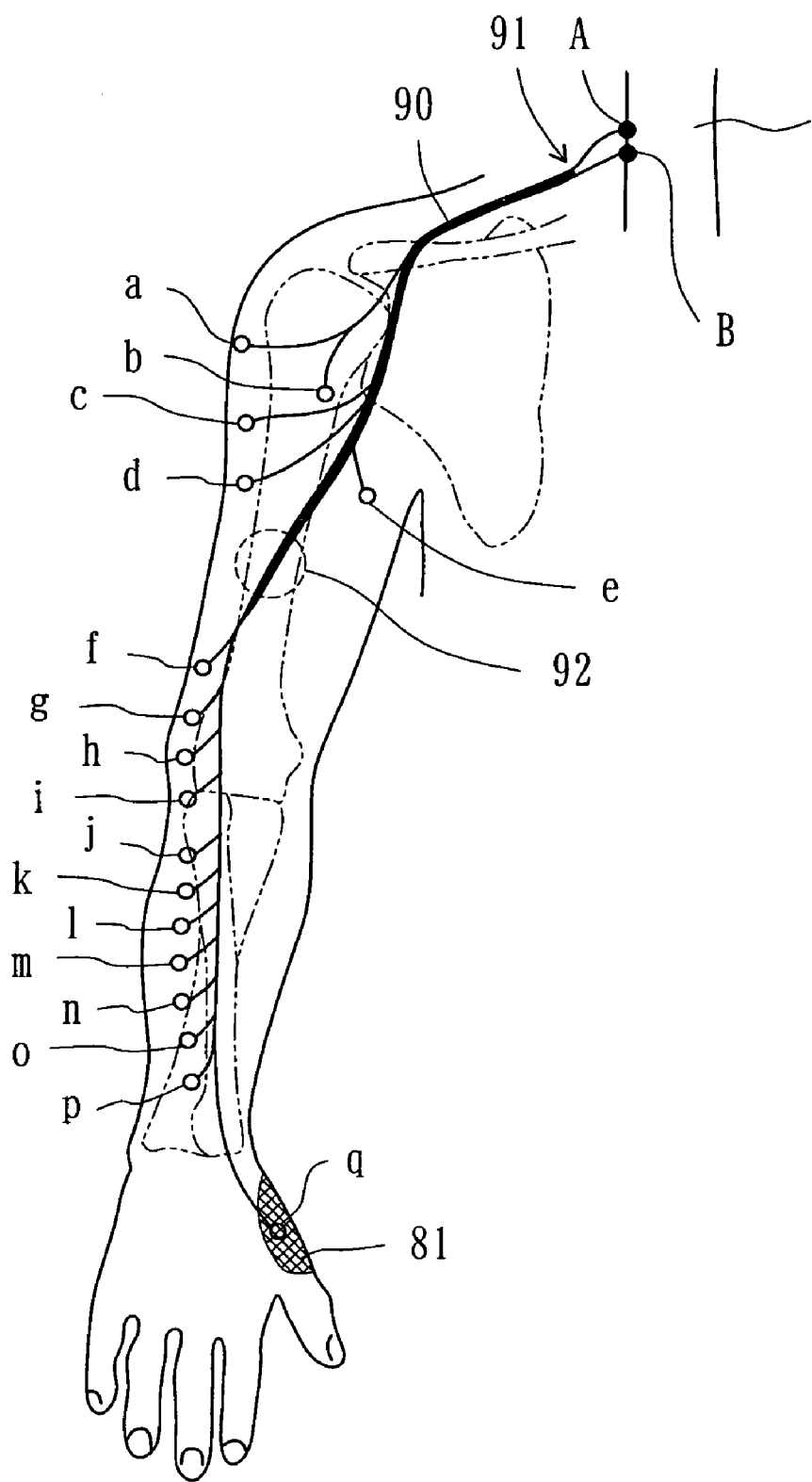
FIG. 30 is a view showing an example of a whole nerve pathway diagram with associated nerve pathways indicated therein.

In order to presume more precisely the associated lesion, a finding due to an electromyogram is added. In this case, "yes" or "no" as to abnormality in the electromyogram is input to the electromyogram finding data input column 72 in a data input screen page (see FIG. 27) displayed on the display 4. Now, for instance, it is supposed with reference to FIG. 30 that normal findings in the electromyogram are observed in an extent from the reference character a (deltoideus muscle) to the reference character e (musculi anconeus) in a direction from the spinal cord S to a peripheral region, but an abnormal finding in the electromyogram is observed at the reference character f (musculi brachioradialis). In this case, in FIG. 30, an associated nerve pathway part for connecting spinal roots A and B relating to the a (deltoideus muscle) to the e (musculi anconeus) is removed from the associated nerve pathway 90 displayed in the whole nerve pathway diagram. Then, an area 92 is detected in the remaining part as a region 92 where associated nerve pathways overlap the most frequently with each other, so that it is presumed to be an associated lesion, and it is displayed in the whole nerve pathway diagram.

The above-mentioned embodiment relates to a system wherein an associated nerve pathway is displayed by utilizing a computer in a whole nerve pathway diagram or a nerve pathway cut surface from a neural finding with respect to a patient. In this respect, an associated nerve pathway is the same as an anatomical functional pathway of a whole nerve pathway containing motor and perception pathways, after all. Accordingly, the present invention is also applicable for learning of neuroanatomy.

Figure 17:
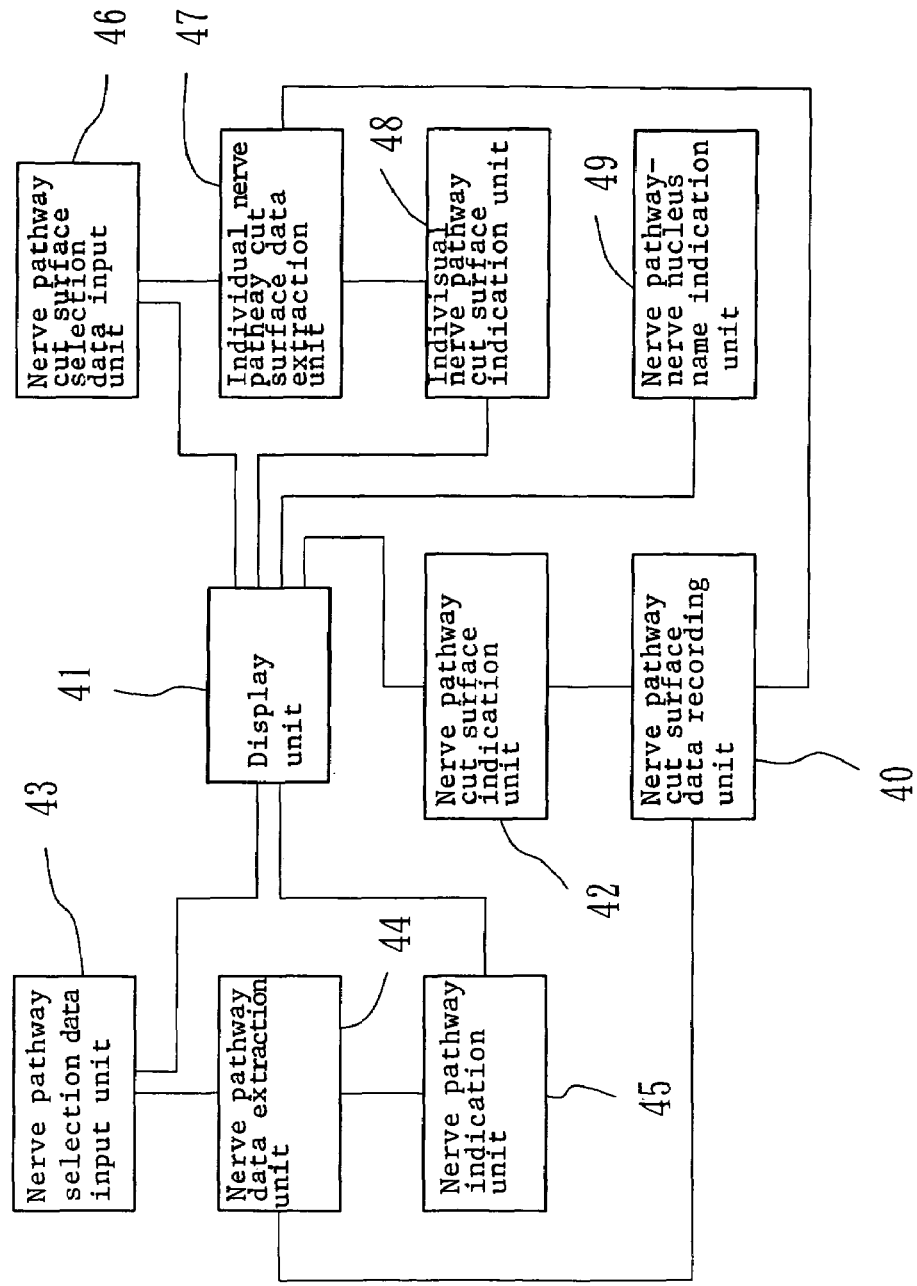
FIG. 17 is a block diagram of a neuroanatomy learning system according to an embodiment of the present invention.

FIG. 17 is a block diagram illustrating a neuroanatomy learning system according an embodiment of the present invention. The neuroanatomy learning system of the present invention utilizes a computer and, as shown in FIG. 17, which is provided with a second data recording part 40 for recording data of cut surfaces in at least one region of cerebrum and mesencephalon, at least one region of pons, at least one region of medulla oblongata, and at least one region of spinal cord, respectively, in a whole pathway diagram, a display 41, and a nerve pathway cut surface indication part 42 for displaying cut surfaces of at least one region of the cerebrum and the mesencephalon, at least one region of the pons, at least one region of the medulla oblongata, at least one region of the medulla oblongata, and at least one region of the spinal cord, respectively, in this order based on the data stored in the second data recording part 40.

In the present embodiment, at least one region of the mesencephalon consists of the upper part of the mesencephalon and the lower part of the mesencephalon, at least one region of the pons consists of the upper, the middle, and the lower parts of the pons, at least one region of the medulla oblongata consists of the upper part, the upper-middle part, the middle, the middle-lower part, and the lower part of the medulla oblongata, and at least one region of the spinal cord consists of a cervical segment, a thoracic segment, and a lumbar segment.

The data stored in the second data recording part 40 contains data of relevant names and positions of nerve nuclei in the cut surfaces, relevant connection relations in the nerve nuclei, and data of curves or straight lines representing nerve fascicles for connecting relevant nerve nuclei with each other, and names of relevant nerve pathway and positions in the cut surfaces in every cut surfaces.

Figure 18:
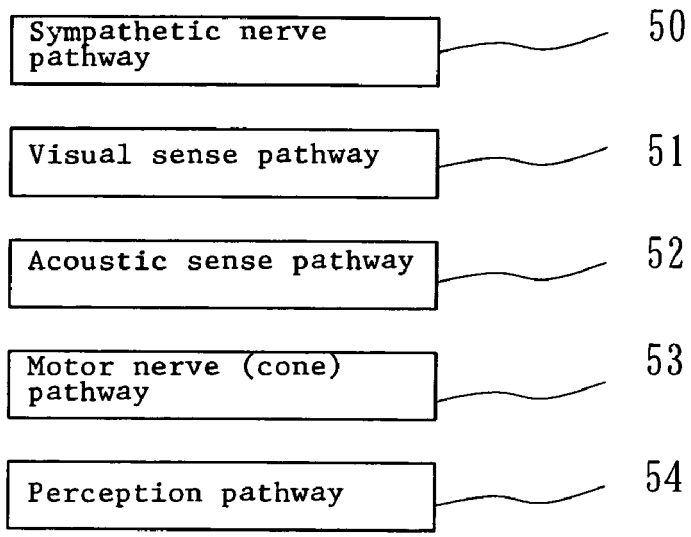
FIG. 18 is a diagram showing an embodiment of a screen page for selection of nerve pathways in the system shown in FIG. 17.

The system of the present invention is further provided with a nerve pathway selection data input part 43 for receiving selection data of nerve pathways to be displayed on the display. FIG. 18 illustrates a nerve pathway selection data input screen page displayed on the display 41 by means of the nerve pathway selection data input part 43. As shown in FIG. 18, the nerve pathway selection data input screen page includes a sympathetic nerve pathway display button 50, a visual sense pathway display button 51, an acoustic sense pathway display button 52, a motor nerve (cone) pathway display button 53, and a perception pathway display button 54 wherein when a desired button is pressed by means of a pointing device such as a mouse, a nerve pathway to be displayed is selected.

The system of the present invention is further provided with a nerve pathway data extraction part 44 for extracting data for drawing relevant nerve pathway from the data stored in the second data recording part 40 based on the data received by the nerve pathway selection data input part 43 in every nerve pathway cut surfaces, and a nerve pathway indication part 45 for displaying relevant nerve pathways in a nerve pathway cut surface displayed by the nerve pathway cut surface indication part 42 based on the data extracted by the nerve pathway data extraction part 44.

FIGS. 19 through 25 are a series of nerve pathway cut surface diagrams which are displayed together on the display in the case when the motor nerve pathway display button 53 is pressed to select a motor nerve pathway in the nerve pathway selection data input screen page of FIG. 18.

Figure 19:
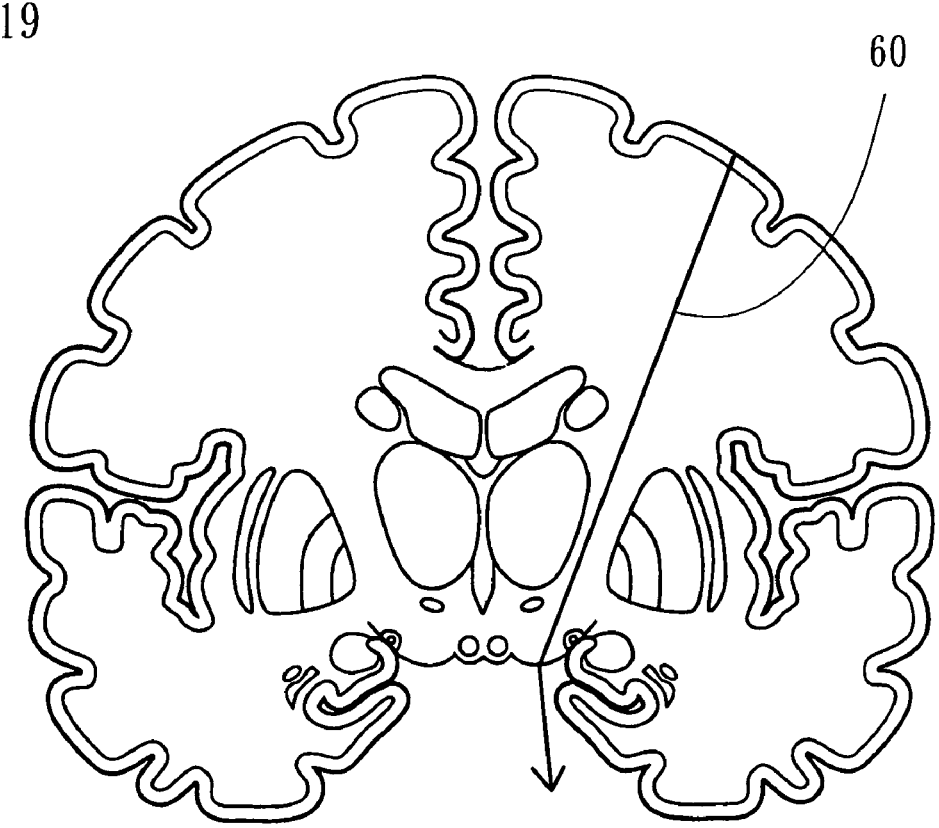
FIG. 19 is a view showing a part of a series of nerve pathway cut surfaces with a nerve pathway indicated therein.
Figure 22:
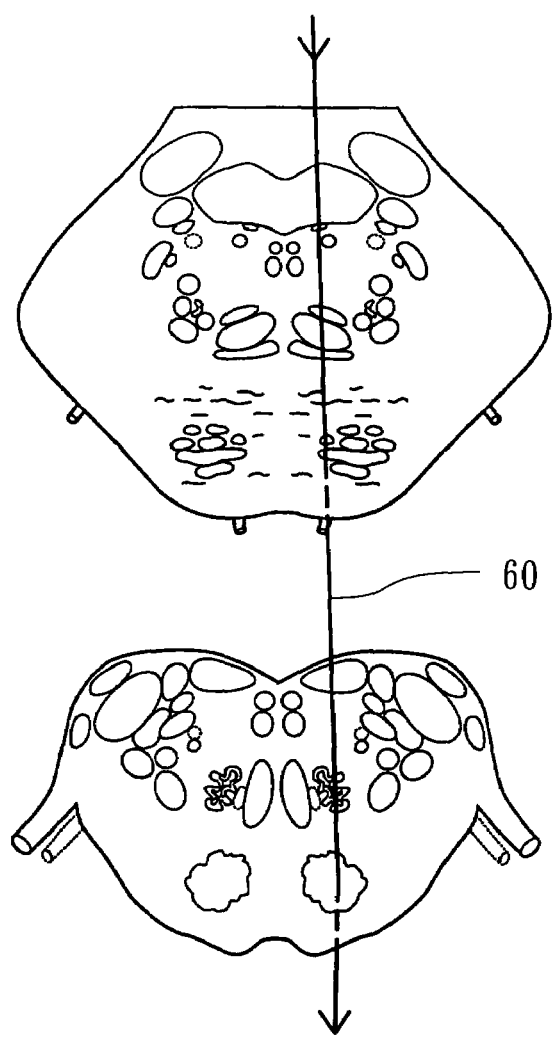
FIG. 22 is a view showing a part of a series of nerve pathway cut surfaces with a nerve pathway indicated therein.
Figure 23:
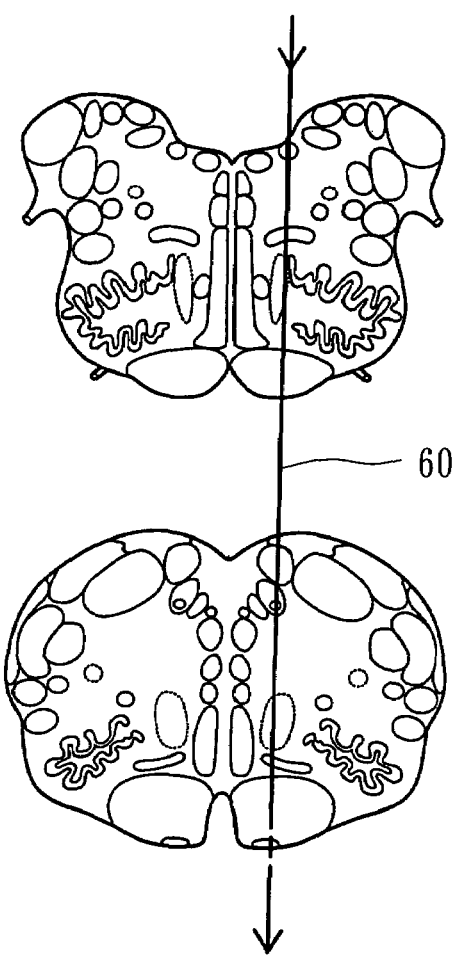
FIG. 23 is a view showing a part of a series of nerve pathway cut surfaces with a nerve pathway indicated therein.
Figure 24:
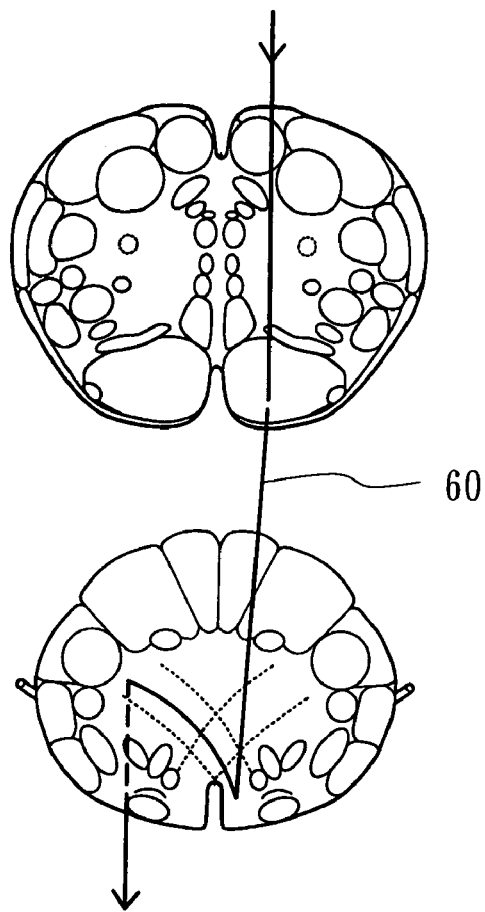
FIG. 24 is a view showing a part of a series of nerve pathway cut surfaces with a nerve pathway indicated therein.
Figure 25:
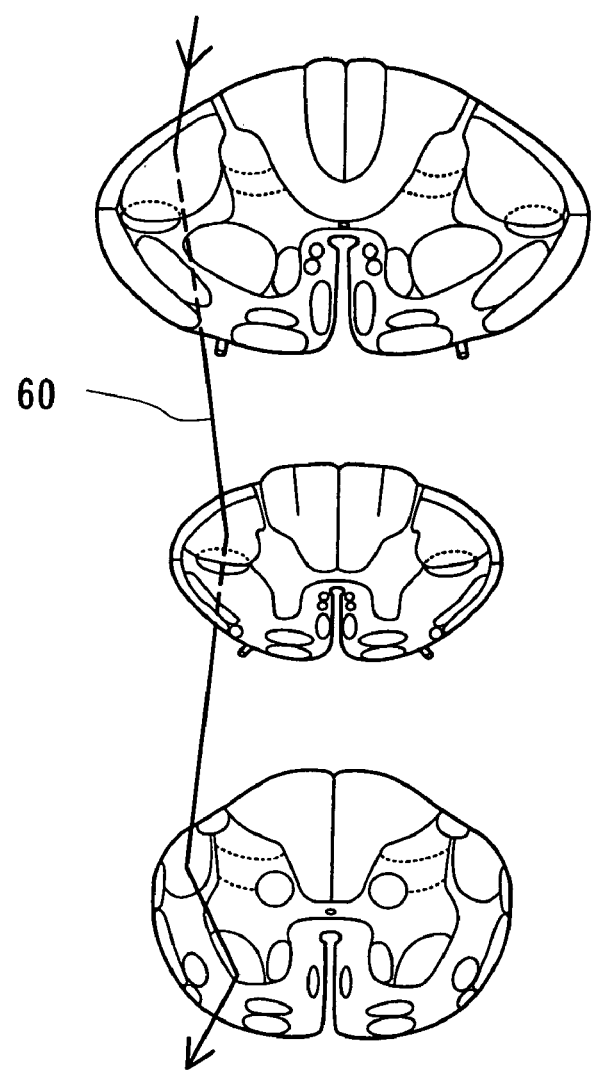
FIG. 25 is a view showing a part of a series of nerve pathway cut surfaces with a nerve pathway indicated therein.

FIG. 19 shows a cerebrum coronary cut surface, and FIG. 20 shows a mesencephalon upper part cut surface following to the underside of the cerebrum coronary cut surface of FIG. 19, and a mesencephalon lower part cut surface following to the underside thereof. FIG. 21 shows a pons upper part cut surface following to the underside of the mesencephalon lower part cut surface of FIG. 20, and a pons middle part cut surface following to the underside thereof, and FIG. 22 shows a pons lower part cut surface following to the underside of the pons middle part cut surface of FIG. 21, and a medulla oblongata upper part cut surface following to the underside thereof. FIG. 23 shows a medulla oblongata upper-middle part cut surface following to the underside of the medulla oblongata upper part cut surface of FIG. 22, and a medulla oblongata middle part cut surface following to the underside thereof, and FIG. 24 shows a medulla oblongata middle-lower part cut surface following to the underside of the medulla oblongata middle part cut surface of FIG. 23, and a medulla oblongata lower part cut surface following to the underside thereof. FIG. 25 shows a cervical segment cut surface following to the medulla oblongata lower part cut surface of FIG. 24, a thoracic segment cut surface following to the underside thereof, and a lumbar segment cut surface following to the underside thereof.

As shown in FIGS. 19 through 25, the motor nerve pathway 20 is displayed in a series of nerve pathway cut surface.

Furthermore, the system of the present invention is provided with a nerve pathway cut surface selection data input part 46 for receiving selection data input for a nerve pathway cut surface which is intended to individually display among the nerve pathway cut surfaces displayed on the display 41 by means of the nerve pathway cut surface indication part 42, an individual nerve pathway cut surface data extraction part 47 for extracting data for drawing a relevant nerve pathway cut surface from the data stored in the second data recording part 40 based on the data received by the nerve pathway cut surface selection data input part 46, an individual nerve pathway cut surface indication part 48 for displaying a relevant nerve pathway cut surface on the display 41 based on the data extracted by the individual nerve pathway cut surface data extraction part 47, and a nerve pathway-nerve nucleus name indication part 49 for displaying a name of a nerve pathway or a nerve nucleus which is selected in the nerve pathway cut surface displayed on the display 41 by means of the individual nerve pathway cut surface indication part 48.

When, for instance, a series of nerve pathway cut surfaces are displayed on the display 41 and any of the cut surfaces is double-clicked by means of a pointing device such as a mouse, selection data for the cut surface selected is input to the nerve pathway cut surface selection data input part 46.

Figure 26:
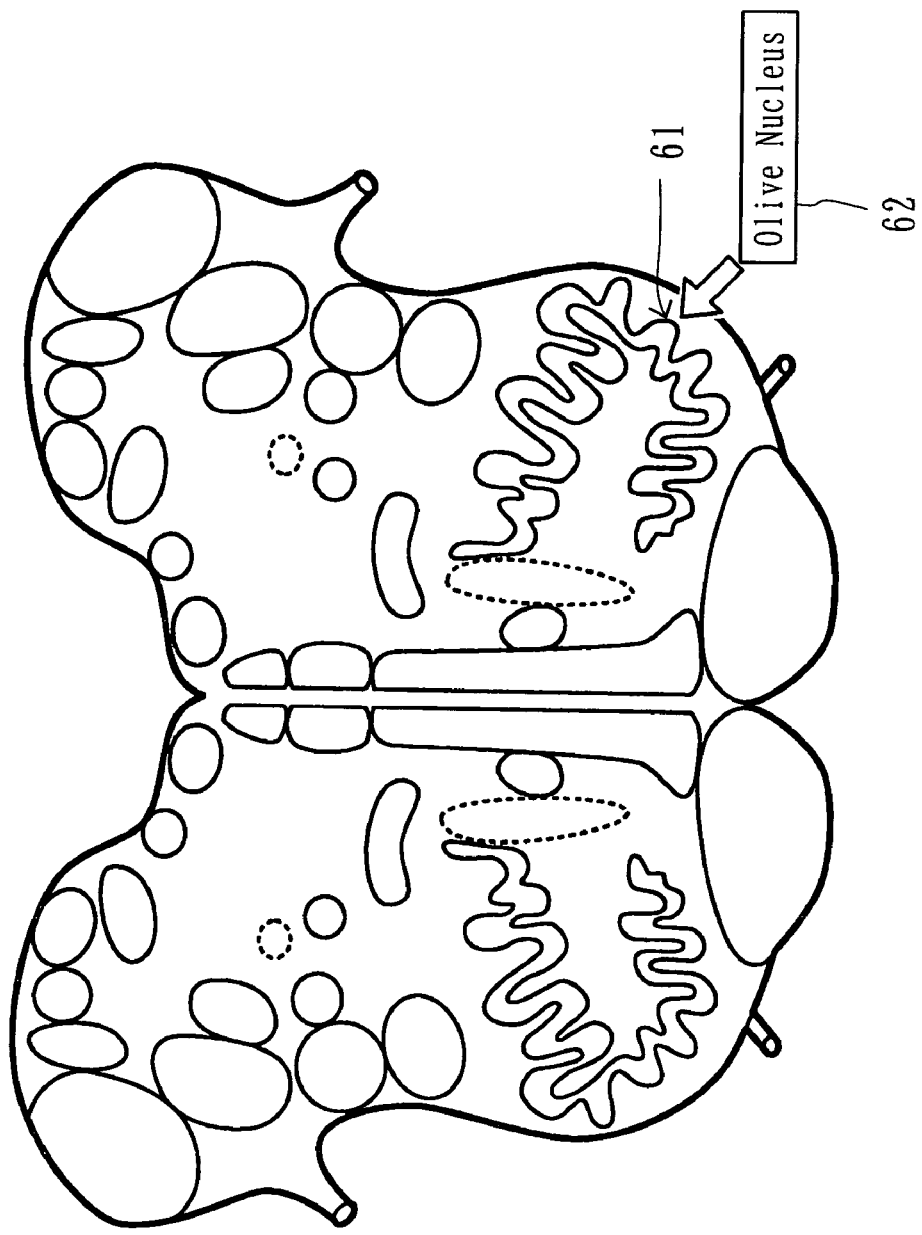
FIG. 26 is a view showing an example of individual enlarged views of the nerve pathway cut surfaces.

Now, when the medulla oblongata upper-middle part cut surface on the upper side in FIG. 23 is selected, the medulla oblongata upper-middle part cut surface is displayed in an enlarged manner on the display 41 as shown in FIG. 26 by means of the individual nerve pathway cut surface indication part 48. On the page screen shown in FIG. 26, when, for embodiment, a position of a region 61 is specified by a pointing device such as a mouse, a name of a corresponding nerve pathway or name of nerve nucleus is displayed in a window 62, and in this figure, a name of nerve nucleus "olive nucleus"

is displayed in the window 62 by means of the nerve pathway-nerve nucleus name indication part 49.

INDUSTRIAL APPLICABILITY

According to the present invention, when a medical physician inputs only data of neural findings to a topical nerve diagnostic system associated nerve pathways are automatically displayed on a display of a computer together with a whole nerve pathway diagram, so that an associated lesion with respect to a neural disorder of a patient is automatically displayed. Thus, the medical physician can give a rapid and correct diagnosis in case of topical nerve diagnosis without relying upon own experience and gut feeling unlike in a conventional manner. Therefore, the present invention contributes remarkably to medical equipment affiliated industries as a kind of diagnosis support system in a topical nerve diagnosis.

Moreover, according to the present invention, a medical student can learn visually positions and mutual physical relationships in a whole nerve pathway diagram of respective nerve pathways in human body, besides positions and names of nerve pathways and nerve nuclei belonging to nerve pathway cut surfaces in every cut surfaces thereof by observing cut surfaces and nerve pathways in a specified region in the whole nerve pathway diagrams displayed sequentially on a display of a computer as well as watching individual enlarged diagrams of the cut surfaces displayed on the display. As a result, the medical student can understand easily and memorize efficiently nerve pathway diagrams and nerve cut surfaces in neuroanatomy. Therefore, the present invention contributes significantly to medical educational material affiliated industries as an assisting means for medical education relating to neuroanatomy.

The invention claimed is:

1. A topical nerve diagnostic system with the use of a computer, comprising:
    a first data recording part storing data of a whole nerve pathway diagram;
    a first input part for receiving input data of neural findings;
    a first data extraction part configured for extracting, from the data stored in said first data recording part, data for drawing associated nerve pathways related to abnormal neural findings according to neural finding data inputted through said first input part;
    a display;
    a whole nerve pathway indication part configured for displaying a whole nerve pathway diagram on said display based on the data stored in said first data recording part;
    an associated nerve pathway indication part configured for drawing, based on the data extracted by said first data extraction part, associated nerve pathways in the whole nerve pathway diagram displayed on said display
    an associated lesion estimation and indication part configured for calculating, based on the associated nerve pathways drawn on said display by said associated nerve pathway indication part, a position of each of associated lesions and indicating the associated lesions in the whole nerve pathway diagram;
    wherein the data stored in said first data recording part contains data of names of nerve nuclei and positions thereof in the whole nerve pathway diagram, data of connection relations of the nerve nuclei, and data of curves and straight lines representing nerve fascicles which connect the nerve nuclei with each other;
    wherein said first data extraction part is configured to extract, for each of abnormal findings, from said first data recording part, data of names of associated nerve nuclei and positions thereof in the whole nerve pathway diagram, data of connection relations of the associated nerve nuclei, and data of curves and straight lines representing nerve fascicles which connect the associated nerve nuclei with each other; and
    wherein said associated lesion estimation and indication part is configured to detect a region where associated nerve pathways displayed on said display intersect with each other and a region where associated nerve pathways approach each other at closest distance, and presumes the detected regions to be associated lesions so as to display the associated lesions in said whole nerve pathway diagram on said display;
    a second data recording part storing cut surface data of specified regions of the whole nerve pathway diagram;
    a second input part for receiving input data of selection of which region of the whole nerve pathway diagram is to be indicated as a cut surface on said display;
    a second data extraction part configured for extracting, from the data stored in said second data recording part, data for drawing associated nerve pathways related to abnormal neural findings in a cut surface of a specified region according to the data inputted through said second input part and the data inputted through said first input part;
    a nerve pathway cut surface indication part configured for extracting, from the data stored in said second data recording part, associated cut surface data according to the data inputted through said second input part so as to display the associated cut surface;
    a second associated nerve pathway indication part configured for drawing, based on the data extracted by said second data extraction part, associated nerve pathways in the nerve pathway cut surface displayed by said nerve pathway cut surface indication part;
    a second associated lesion estimation and indication part configured for calculating, based on the associated nerve pathways displayed on said display by said second associated nerve pathway indication part, a position of each of associated lesions in the associated cut surface so as to display the associated lesions in the associated cut surface.

2. The topical nerve diagnostic system according to claim 1, wherein the data stored in said second data recording part contains, for all cut surfaces, data of names of nerve nuclei and positions thereof in the cut surface, data of connection relations of nerve nuclei, and data of curves and straight lines representing nerve fascicles which connect the associated nerve nuclei with each other.

3. The topical nerve diagnostic system according to claim 2, wherein said second data extraction part is configured to extract, for each of abnormal findings, from said second data recording part, data of names of associated nerve nuclei and positions thereof in the cut surface, data of connection relations of the associated nerve nuclei, and data of curves and straight lines representing nerve fascicles which connect the associated nerve nuclei with each other second data recording part.

4. The topical nerve diagnostic system according to claim 1, wherein second associated lesion estimation and indication part is configured to detect a region where associated nerve pathways displayed on said display intersect with each other and a region where associated nerve pathways approach each other at closest distance, and presumes the detected regions to be associated lesions so as to display the associated lesions in the cut surface.

5. The topical nerve diagnostic system according to claim 1, further comprising a screen page switchover part configured for switching over a screen page between a screen page of the whole nerve pathway diagram and a screen page of a cut surface of a specified region of the whole nerve pathway diagram.

6. The topical nerve diagnostic system according to claim 1, wherein said neural findings include oculomotor restriction, inferior oculomotor restriction, jaw reflex acceleration, impaired facial tactual sensation, impaired facial pain/temperature sensation, corneal areflexia, lack of exterior oculomotor restriction, upper facial paralysis, lower facial paralysis, impaired taste, lowered pharyngeal reflex/swallowing difficulty, impaired pharyngeal sound dysphemia, lingual muscle paralysis/impaired lingual sound dysphemia, sternocleidomastoid paralysis, impaired upper limb pain/temperature sensation, impaired upper limb deep sensation, upper limb motor paralysis, superior limb tendon reflex, impaired trunk pain/temperature sensation, impaired trunk deep sensation, level of impaired trunk deep sensation, impaired lower limb pain/temperature sensation, inferior bathyesthesia disorder, lower limb motor paralysis, inferior limb tendon reflex, and Babinski reflex.

7. The topical nerve diagnostic system according to claim 1, wherein the data stored in said first data recording part contains data of names of spinal roots, muscles and skin areas and positions thereof in the whole nerve pathway diagram, data of connection relations of the spinal roots and the muscles, and data of curves and straight lines representing nerve fascicles which connect the spinal roots with the muscles as well as data of connection relations of the spinal roots and the skin areas, and curves and straight lines which connect the spinal roots with the skin areas.

8. The topical nerve diagnostic system according to claim 7, wherein said first data extraction part is configured to extract, for each of abnormal findings, from said first data recording part data of names of associated spinal roots, associated muscle and associated skin areas and positions thereof in the whole nerve pathway diagram, data of connection relations of the associated spinal roots and the associated muscles, and data of curves and straight lines representing nerve fascicles which connect the associated spinal roots with the associated skin areas as well as data of connection relations of the associated spinal roots and the associated skin areas, and data of curves and straight lines which connect the associated spinal roots with the associated skin areas.

9. The topical nerve diagnostic system according to claim 8, wherein said associated lesion estimation and indication part is configured to detect a region where associated nerve pathways displayed on said display overlap with each other at a highest degree, and presume the detected region to be an associated lesion so as to display the associated lesion in the whole nerve pathway diagram on said display.

10. The topical nerve diagnostic system according to claim 9, further comprising a third associated lesion estimation and indication part configured for removing an associated nerve pathway part from the associated nerve pathways drawn by said associated lesion estimation and indication part in the whole nerve pathway diagram on the display when said first input part receives input data of neural finding of the muscles or the skin areas which are related to the associated nerve pathways said associated nerve pathway part corresponding to nerve fascicles which connect a muscle or a skin area relating to normal finding with the associated spinal roots.

11. The topical nerve diagnostic system according to claim 10, wherein the neural findings include findings with respect to muscle strength related to movement of joints and perception disorder of skin areas.

* * * * *